(12) United States Patent
Yamahara et al.

(10) Patent No.: US 11,389,486 B2
(45) Date of Patent: Jul. 19, 2022

(54) METHOD FOR PRODUCING AMNIOTIC MESENCHYMAL STROMAL CELL COMPOSITION, METHOD FOR CRYOPRESERVING THE SAME, AND THERAPEUTIC AGENT

(71) Applicants: NATIONAL CEREBRAL AND CARDIOVASCULAR CENTER, Suita (JP); FOUNDATION FOR BIOMEDICAL RESEARCH AND INNOVATION AT KOBE, Kobe (JP); HYOGO COLLEGE OF MEDICINE, Nishinomiya (JP); NATIONAL UNIVERSITY CORPORATION HOKKAIDO UNIVERSITY, Sapporo (JP); KANEKA CORPORATION, Osaka (JP)

(72) Inventors: Kenichi Yamahara, Suita (JP); Akihiko Taguchi, Kobe (JP); Toshihiro Soma, Nishinomiya (JP); Shunsuke Ohnishi, Sapporo (JP); Akira Kobayashi, Takasago (JP)

(73) Assignees: NATIONAL CEREBRAL AND CARDIOVASCULAR CENTER, Suita (JP); FOUNDATION FOR BIOMEDICAL RESEARCH AND INNOVATION AT KOBE, Kobe (JP); HYOGO COLLEGE OF MEDICINE, Nishinomiya (JP); NATIONAL UNIVERSITY CORPORATION HOKKAIDO UNIVERSITY, Sapporo (JP); KANEKA CORPORATION, Osaka (JP)

( * ) Notice: Subject to any disclaimer, the term of this patent is extended or adjusted under 35 U.S.C. 154(b) by 263 days.

(21) Appl. No.: 16/508,463

(22) Filed: Jul. 11, 2019

(65) Prior Publication Data
US 2019/0343892 A1 Nov. 14, 2019

Related U.S. Application Data

(63) Continuation of application No. 14/912,662, filed as application No. PCT/JP2014/071546 on Aug. 18, 2014, now Pat. No. 10,441,611.

(30) Foreign Application Priority Data

Aug. 19, 2013 (JP) .................................. 2013-170008
Jun. 25, 2014 (JP) .................................. 2014-130142

(51) Int. Cl.
*A61K 35/50* (2015.01)
*A61K 9/00* (2006.01)
*A61K 35/28* (2015.01)
*A61L 27/38* (2006.01)
*A61L 27/50* (2006.01)
(Continued)

(52) U.S. Cl.
CPC ............ *A61K 35/50* (2013.01); *A61K 9/0019* (2013.01); *A61K 35/28* (2013.01); *A61L 27/3834* (2013.01); *A61L 27/50* (2013.01); *C12N 5/0605* (2013.01); *C12N 5/0668* (2013.01); *C12N 5/0669* (2013.01); *A61L 2300/64* (2013.01); *C12N 2506/03* (2013.01)

(58) Field of Classification Search
CPC ...... A61K 35/50; A61K 9/0019; A61K 35/28; C12N 5/0668; C12N 5/0605; A61L 27/3834; A61L 27/50
See application file for complete search history.

(56) References Cited

U.S. PATENT DOCUMENTS

| 7,109,032 B2 | 9/2006 | Cancedda |
| 2004/0121300 A1 | 6/2004 | Frey et al. |

(Continued)

FOREIGN PATENT DOCUMENTS

| CN | 101501185 A | 8/2009 |
| CN | 102282252 A | 12/2011 |

(Continued)

OTHER PUBLICATIONS

Heazlewood et al., "Optimal tissue sources of mesenchymal stromal cells for clinical applications." In: Chase and Venmuri eds. Mesenchymal stem cell therapy (New York, Humana Press, 2013), pp. 355-372. (Year: 2013).*
Dispase II (neutral protease, grade II). Datasheet [online]. Roche Diagnostics, GmBH, 2010 [retrieved on Sep. 29, 2021], Retrieved from the Internet: <URL: https://www.maokangbio.com/upload/admin/file/2017/06/13/1497366594240.pdf>. (Year: 2010).*
European Office Action dated Aug. 5, 2019, in European Patent Application No. 14837352.5.
(Continued)

*Primary Examiner* — Kara D Johnson
(74) *Attorney, Agent, or Firm* — Oblon, McClelland, Maier & Neustadt, L.L.P.

(57) ABSTRACT

An object of the present invention is to provide a method for producing a mesenchymal stromal cell composition, comprising conveniently and aseptically separating high-purity amnion-derived MSCs by performing enzyme treatment only once. According to the present invention, the following are provided: a method for producing a mesenchymal stromal cell composition, comprising: performing enzyme treatment of an amnion with collagenase and thermolysin and/or dispase; and filtering the enzyme-treated amnion through a mesh; a method for producing a cryopreserved mesenchymal stromal cell composition; and a therapeutic agent comprising as an active ingredient the mesenchymal stromal cell composition for a disease selected from graft-versus-host disease, inflammatory bowel disease, systemic lupus erythematosus, liver cirrhosis, or radiation enteritis.

17 Claims, 12 Drawing Sheets

(51) Int. Cl.
    C12N 5/073    (2010.01)
    C12N 5/0775   (2010.01)
    C12N 5/077    (2010.01)

(56) References Cited

U.S. PATENT DOCUMENTS

| | | | |
|---|---|---|---|
| 2008/0226595 | A1 | 9/2008 | Edinger et al. |
| 2010/0221268 | A1 | 9/2010 | Parolini |
| 2011/0206776 | A1 | 8/2011 | Tom et al. |
| 2011/0212063 | A1 | 9/2011 | Tom et al. |
| 2011/0212064 | A1 | 9/2011 | Jansen et al. |
| 2011/0212065 | A1 | 9/2011 | Jansen et al. |
| 2011/0212158 | A1 | 9/2011 | Tom et al. |
| 2011/0256202 | A1 | 10/2011 | Tom |
| 2014/0037598 | A1 | 2/2014 | Jansen et al. |
| 2014/0127177 | A1 | 5/2014 | Tom et al. |
| 2014/0127317 | A1 | 5/2014 | Jansen et al. |
| 2014/0140966 | A1 | 5/2014 | Tom et al. |
| 2014/0294777 | A1 | 10/2014 | Tom et al. |
| 2014/0301986 | A1 | 10/2014 | Tom et al. |

FOREIGN PATENT DOCUMENTS

| | | | |
|---|---|---|---|
| CN | 103356710 | A | 10/2013 |
| JP | 2000-201672 | A | 7/2000 |
| JP | 2006-51 4653 | A | 5/2006 |
| JP | 2006-514653 | A | 5/2006 |
| JP | 3934539 | B2 | 3/2007 |
| JP | 4330995 | B2 | 6/2009 |
| JP | 2010-518096 | A | 5/2010 |
| JP | 2010-518096 | A5 | 5/2010 |
| JP | 2010-530214 | A | 9/2010 |
| JP | 2011-501960 | | 1/2011 |
| JP | 2012-500021 | A | 1/2012 |
| WO | WO 03/042405 | A2 | 5/2003 |
| WO | WO 2004/058323 | A2 | 7/2004 |
| WO | WO 2008/100498 | A2 | 8/2008 |
| WO | WO 2008/109063 | A2 | 9/2008 |
| WO | WO 2008/151846 | A2 | 12/2008 |
| WO | WO 2009/058365 | A1 | 5/2009 |
| WO | WO 2010/021714 | A2 | 2/2010 |
| WO | WO 2010/059828 | A1 | 5/2010 |
| WO | WO 2011/021618 | A1 | 2/2011 |
| WO | 2013/012698 | A1 | 1/2013 |

OTHER PUBLICATIONS

Chiho Ikebe et al., Mesenchymal Stem Cells for Regenerative Therapy: Optimization of Cell Preparation Protocols, Hindawi Publishing Corporation, BioMed Research International, vol. 2014, Article ID 951512, 11 pages, http://dx.doi.org/10.1155/2014/951512.

C. Bettina Portmann-Lanz, et al., "Placental Mesenchymal Stem Cells as Potential Autologous Graft for Pre- and Perinatal Neuroregeneration" American Journal of Obstetrics and Gynecology, Elsevier, 2006, pp. 664-673.

Fabio Marongiu, et al., "Isolation of Amniotic Mesenchymal Stem Cells" Current Protocols in Stem Cell Biology, Unit 1E.5, 2010, pp. 1E.5.1-1E.5.11.

Maddalena Soncini, et al., "Isolation and Characterization of Mesenchymal Cells from Human Fetal Membranes" Journal of Tissue Engineering and Regenerative Medicine, 2007, pp. 296-305.

Shin Ishikane, et al., "Allogeneic Injection of Fetal Membrane-Derived Mesenchymal Stem Cells Induces Therapeutic Angiogenesis in a Rat Model of Hind Limb Ischemia" Stem Cells, 2008, pp. 2625-2633.

Makiko Ohshima, et al., "Systemic Transplantation of Allogenic Fetal Membrane-Derived Mesenchymal Stem Cells Suppresses Th1 And Th17 T Cell Responses in Experimental Autoimmune Myocarditis" Journal of Molecular and Cellular Cardiology, Elsevier, 2012, pp. 420-428.

Akie Kikuchi-Taura, et al., "Human Umbilical Cord Provides A Significant Source of Unexpanded Mesenchymal Stromal Cells" Informa Healthcare, 2012, pp. 441-450.

Office Action dated Sep. 27, 2016 in Japanese Patent Application No. 2014-130142.

Kazutaka Sunami, et al., "Simplified Method for Cryopreservation of Hematopoetic Stem Cells Using CP-1," Low Temp. Med., vol. 24, No. 4, (1998), pp. 171-174. (with english abstract).

International Search Report and Written Opinion of the International Searching Authority dated Nov. 11, 2014 in PCT/JP2014/071546.

International Preliminary Report on Patentability and Written Opinion of the International Searching Authority dated Mar. 3, 2016 in PCT/JP2014/071546.

International Preliminary Report on Patentability and Written Opinion of the International Searching Authority dated Mar. 3, 2016 in PCT/JP2014/071546 (submitting English translation).

Grozdana Bilic, et al., "In Vitro Lesion Repair by Human Amnion Epithelial and Mesenchymal Cells" American Journal of Obstetrics and Gynecology, Elsevier, 2004, pp. 87-92.

Massimo Dominici, et al., "Minimal Criteria for Defining Multipotent Mesenchymal Stromal Cells. The International Society for Cellular Therapy Position Statement" International Society for Cellular Therapy, vol. 8, No. 4, 2006, pp. 315-317.

Yahaira Naaldijk, et al., "Effect of Different Freezing Rates During Cryopreservation of Rat Mesenchymal Stem Cells Using Combinations of Hydroxyethyl Starch and Dimethylsulfoxide" BMC Biotechnology, 2012, pp. 1-10.

European Office Action dated Mar. 6, 2018 in European Patent Application No. 14837352.5, citing document AX therein, 5 pages.

Stiff, P.J., et al., "Unfractionated Human Marrow Cell Cryopreservation Using Dimethylsulfoxide and Hydroxyethyl Starch", Cryobiology, XP055454230, vol. 20, Jan. 1, 1983, pp. 17-24.

Duijvestein et al., Autologous bone marrow-derived mesenchymal stromal cell treatment for refractory luminal Crohn's disease: results of a phase I study. Gut, vol. 59 (2010) pp. 1662-1669.

Soncini et al., Isolation and characterization of mesenchymal cells from human fetal membranes. Journal of Tissue Engineering and Regenerative Medicine. vol. 1 (2007) pp. 296-305.

R. Ian Freshney., "Cryopreservation." In: Culture of Animal Cell: A Manual of Basic Technique and Specialized Applications. (Hoboken, NJ, John Wiley & Sons, Inc., 2010), pp. 317-334. QH585.2.F74 2010.

Extended European Search Report dated Apr. 1, 2017 in Patent Application No. 14837352.5.

Jeong Hee Moon et al., "Successful Vitrification Of Human Amnion-Derived Mesenchvmal Stem Cells", Human Reproduction vol. 23, No. 8, XP007911987, Jan. 1, 2008, pp. 1760-1770.

Jun Hayakawa et al., "5% Dimethyl Sulfoxide (DMSO) and Pentastarch Improves Cryopreservation Of Cord Blood Cells Over 10% DMSO", Transplantation And Cellular Engineering, Transfusion, vol. 50, No. 10, XP055329488, Oct. 12, 2010, pp. 2158-2166.

Felipe de Lara Janz et al.,"Evaluation of Distinct Freezing Methods and Cryoprotectants for Human Amniotic Fluid Stem Cells Cryopreservation", Journal of Biomedicine and Biotechnology, vol. 53, No. 6, XP055329520, Jan. 1, 2012, Article ID 649353, 10 pages.

Charles J. Hunt, "Cryopreservation of Human Stem Cells for Clinical Application: A Review", Transfusion Medicine and Hemotherapy, vol. 38, No. 2, XP055236379, Jan. 1, 2011, pp. 107-123.

Jacob Hanna et al: "Preservation of stem cells", Organogenesis, vol. 5, No. 3, XP055321573, Sep. 1, 2009, pp. 134-137.

Don Finley: "New Products Cell Freezing Media and Reagents ECACC Cell Lines Protocol for the Cryopreseravtion of Cell Lines Cryoware Cryopreservation Biofiles Biofilescontents Introduction 3", vol. 5, No. 4, XP055329587, Jan. 1, 2010, 24 pages.

Y. Naaldijk et al., "Cryopreservation Of Human Umbilical Cord-Derived Mesenchymal Stem Cells In Complex Sugar Based Cryoprotective Solutions", Journal of Biotechnology Letters, vol. 4, Issue 2, 2013, pp. 95-99.

A. Stolzing et al: "Hydroxyethylstarch in Cryopreservation—Mechanisms, Benefits and Problems", Transfusion And Apheresis Science, vol. 46, No. 2, XP055241323, Apr. 1, 2012, pp. 137-147.

(56) References Cited

OTHER PUBLICATIONS

Office Action dated Sep. 22, 2017 in European Parent Application No. 14837352.5.
Office Action dated Sep. 4, 2018 in Japanese Patent Application No. 2014-130142 with English translation, citing documents AO, AP, AQ, AS, AT, and AX therein, 9 pages.
Combined Office Action and Search Report dated Sep. 19, 2018 in Chinese Patent Application No. 201480046241.8 (with English translation of the Office Action and English translation of categories of cited documents), citing documents AO-AQ therein, 19 pages.
Office Action dated Sep. 4, 2018 in Japanese Patent Application No. 2014-130142 with English Translation, 9 pages.
Ohgushi2009, "Biochemistry", 2009, vol. 81, No. 2, pp. 99-104.
Combined Office Action and Search Report dated Sep. 19, 2018 in Chinese Patent Application No. 201480046241.8 (with English translation of the Office Action and English translation of categories of cited documents), 19 pages.
Japanese Office Action dated Dec. 4, 2018 in Japanese Patent Application No. 2014-130142 (with unedited computer generated English translation), 8 pages.

\* cited by examiner

[Fig. 1]
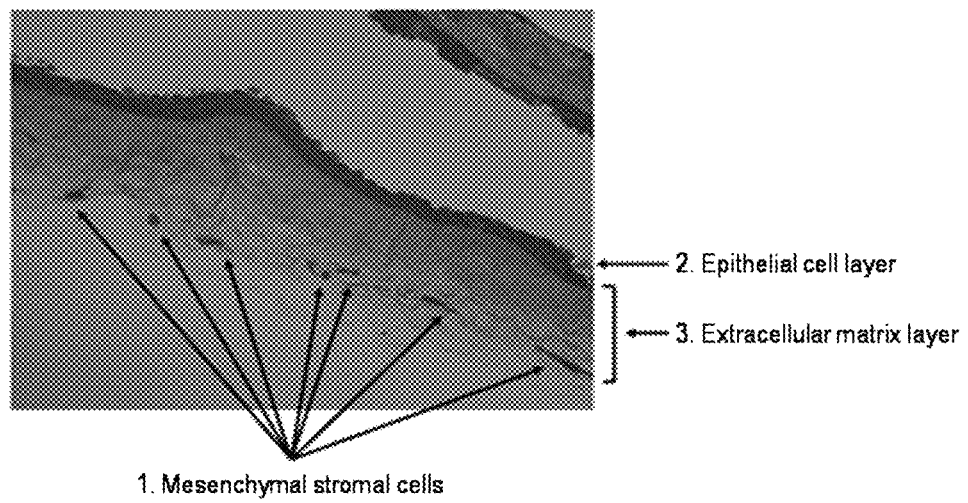
[Fig. 2]
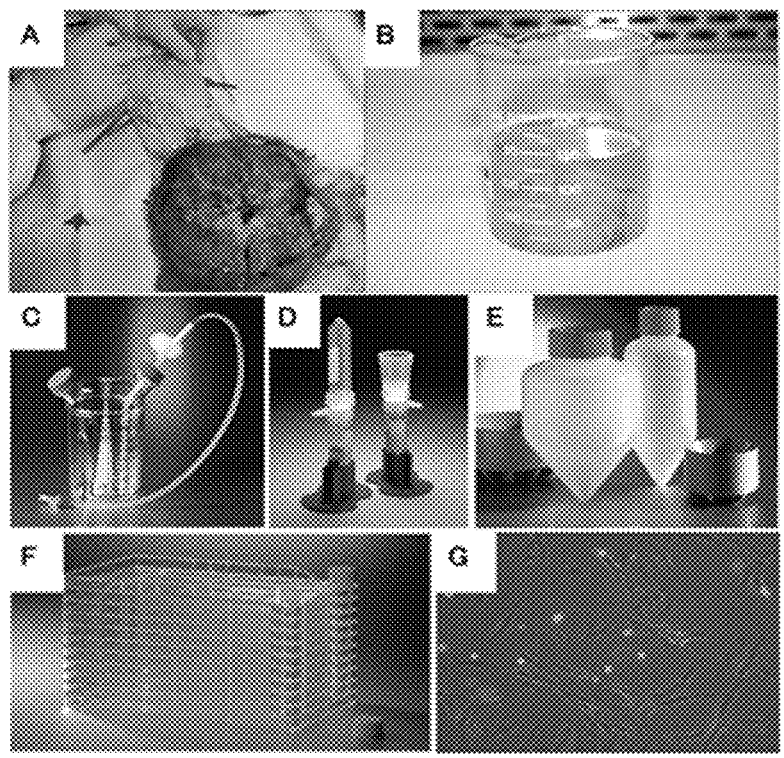

[Fig. 3]
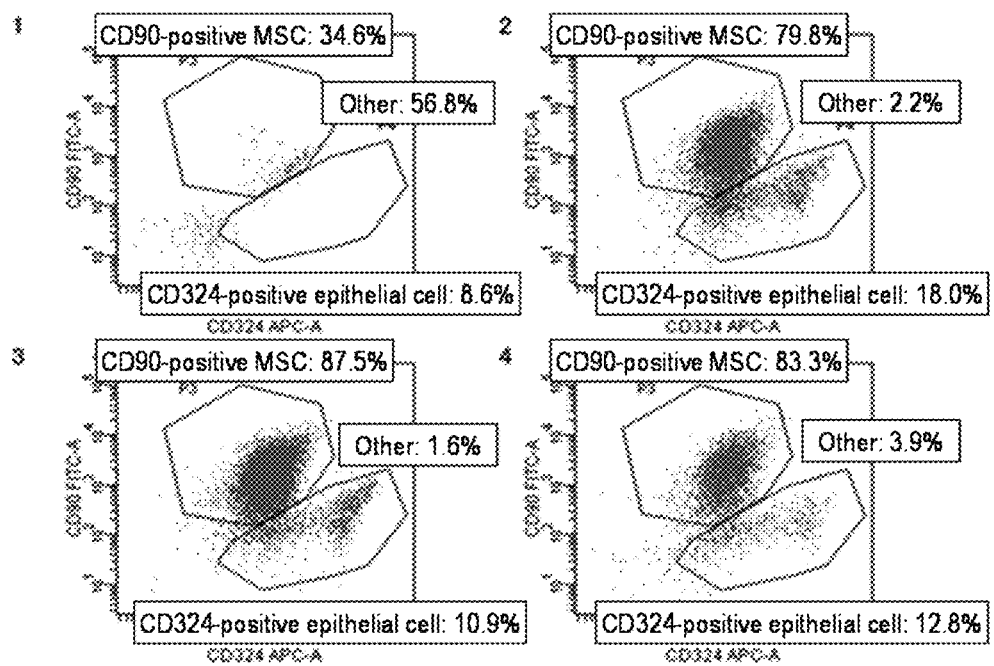
[Fig. 4]
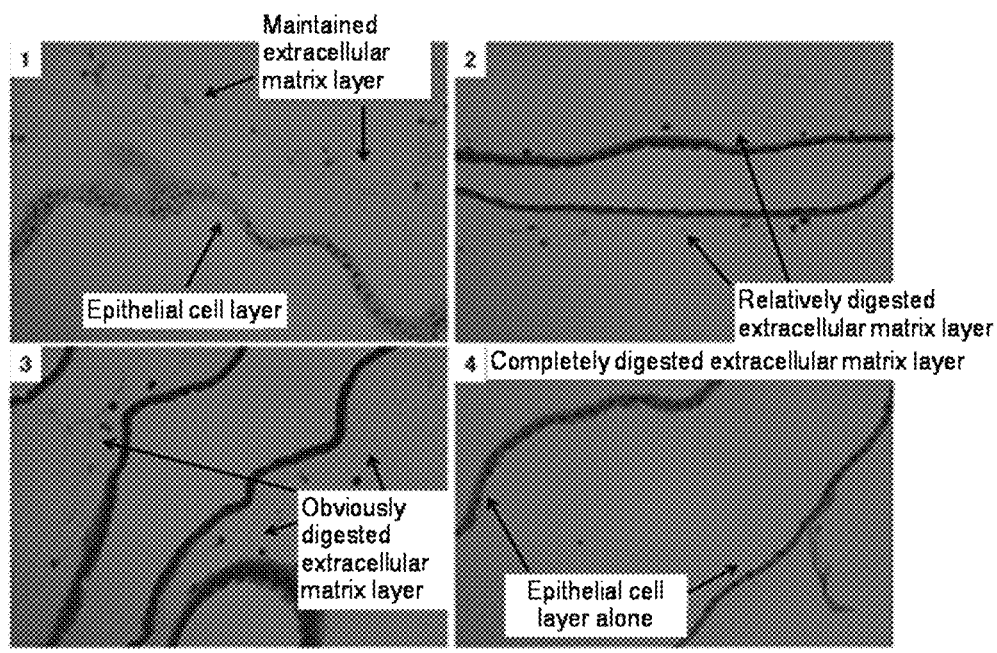

[Fig. 5]
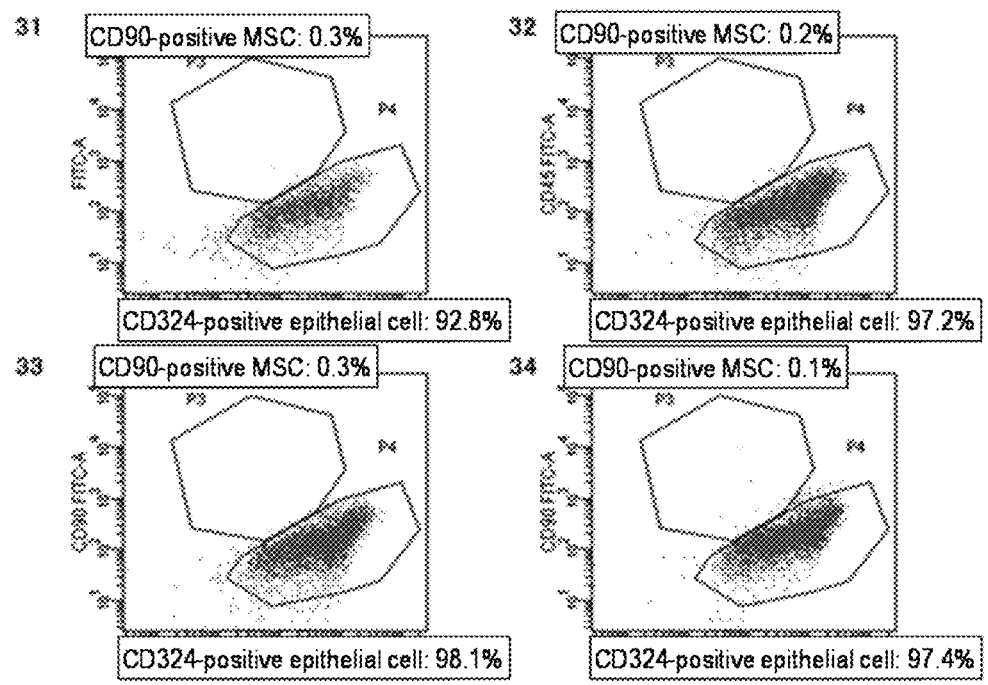
[Fig. 6]
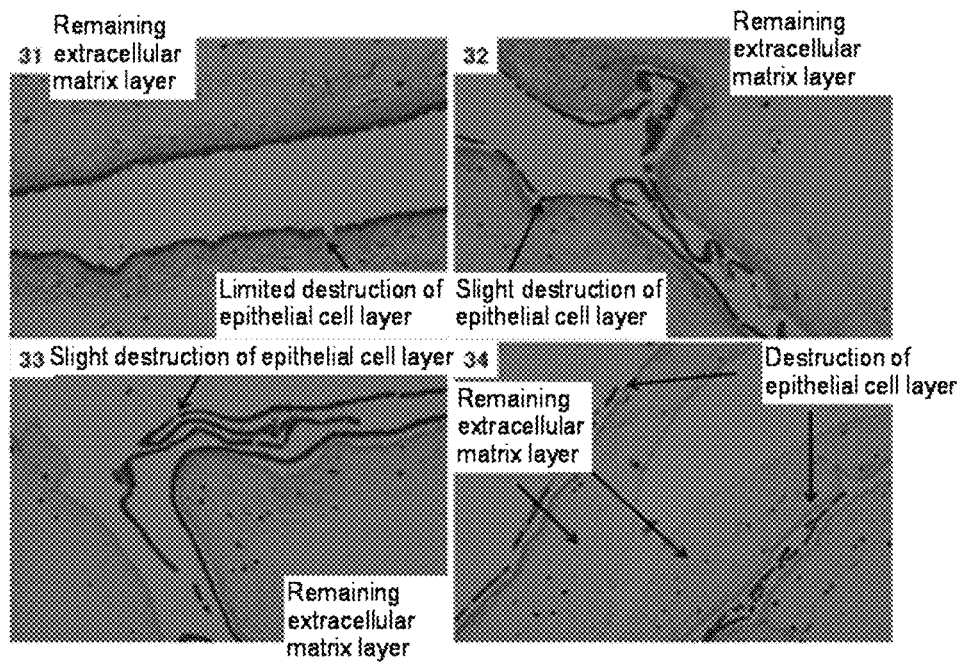

[Fig. 7]
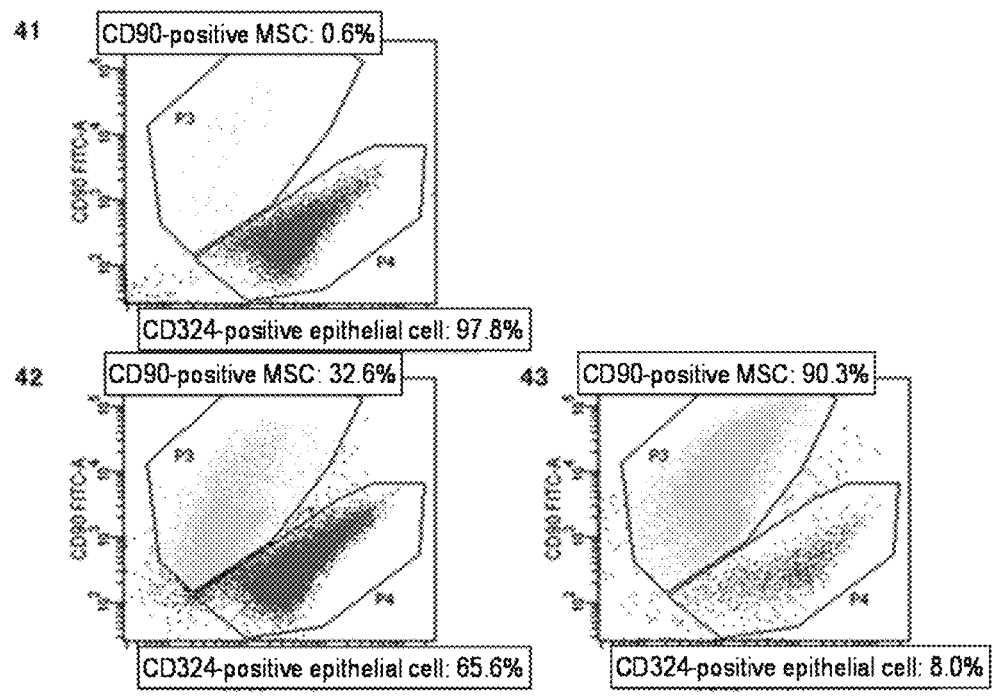
[Fig. 8]
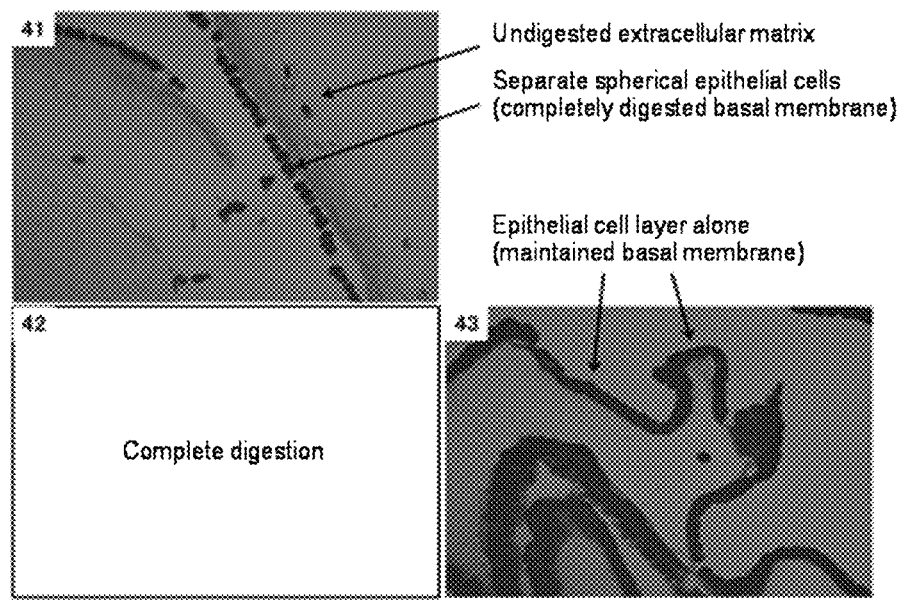

[Fig. 9]
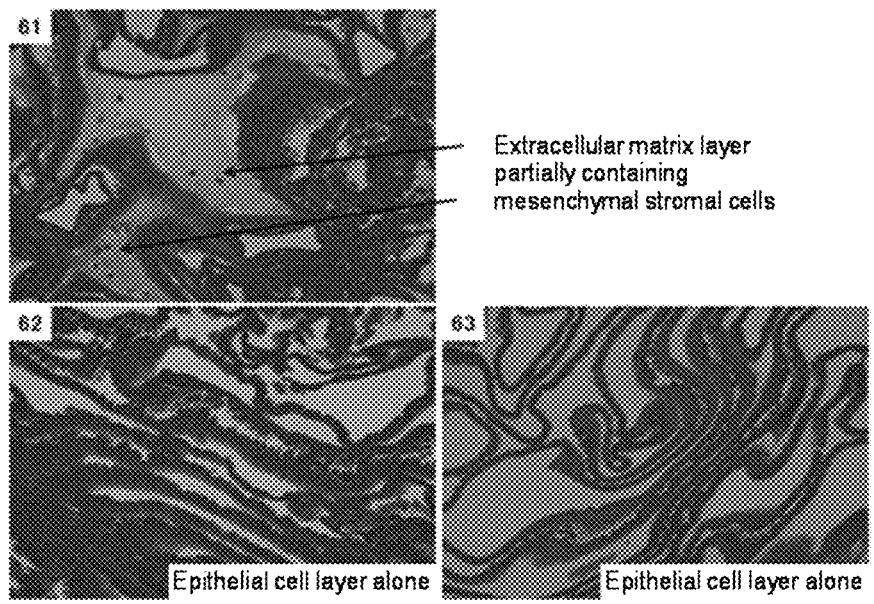
[Fig. 10]
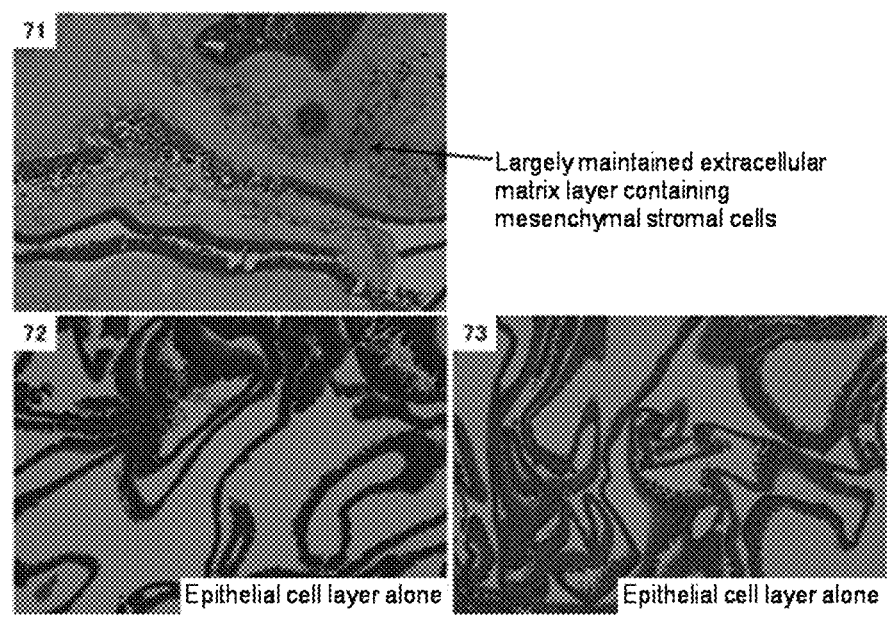

[Fig. 11]
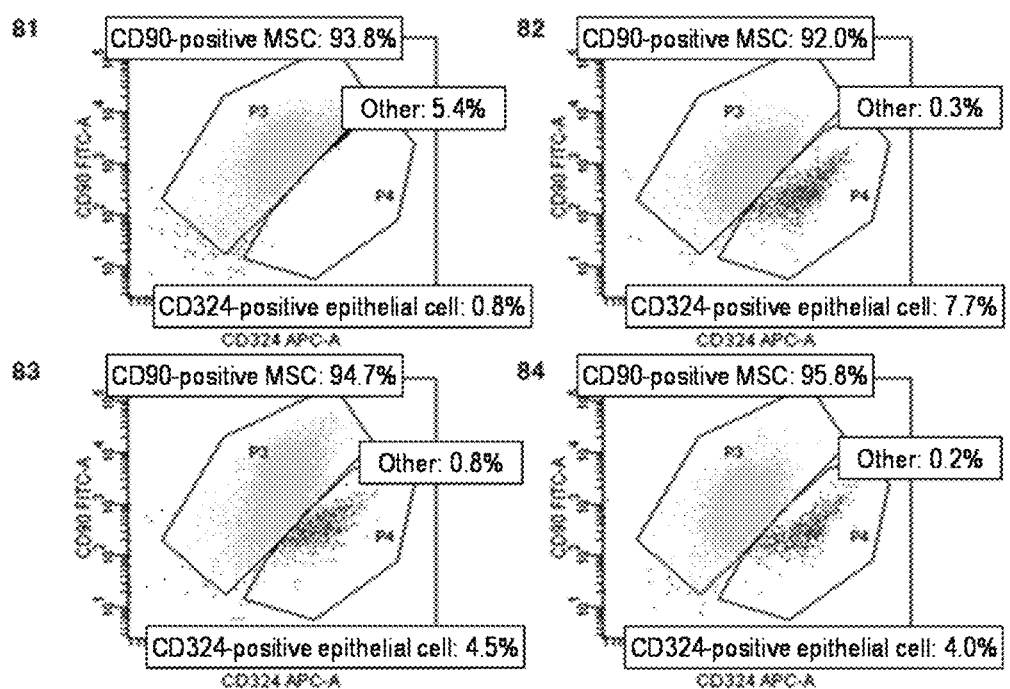

[Fig. 12]
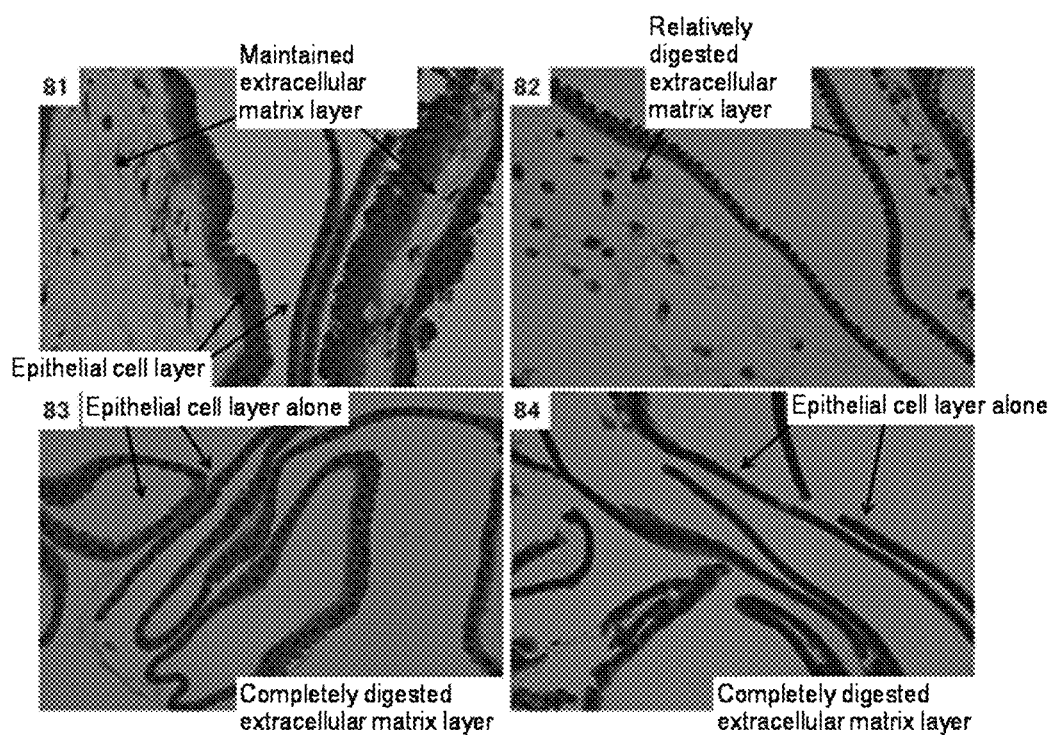

[Fig. 13]
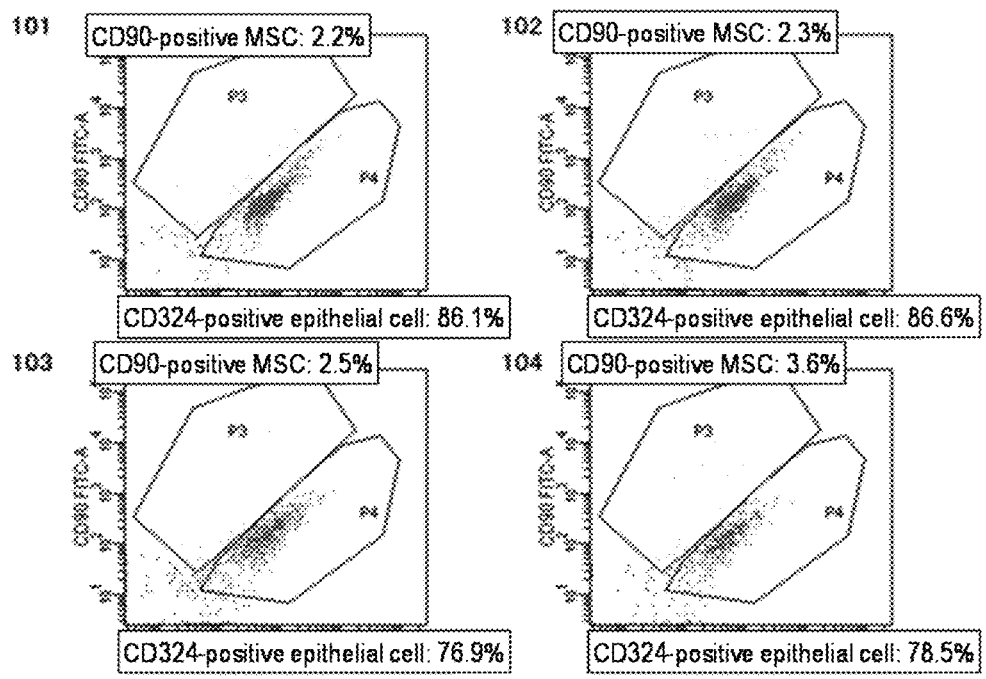
[Fig. 14]
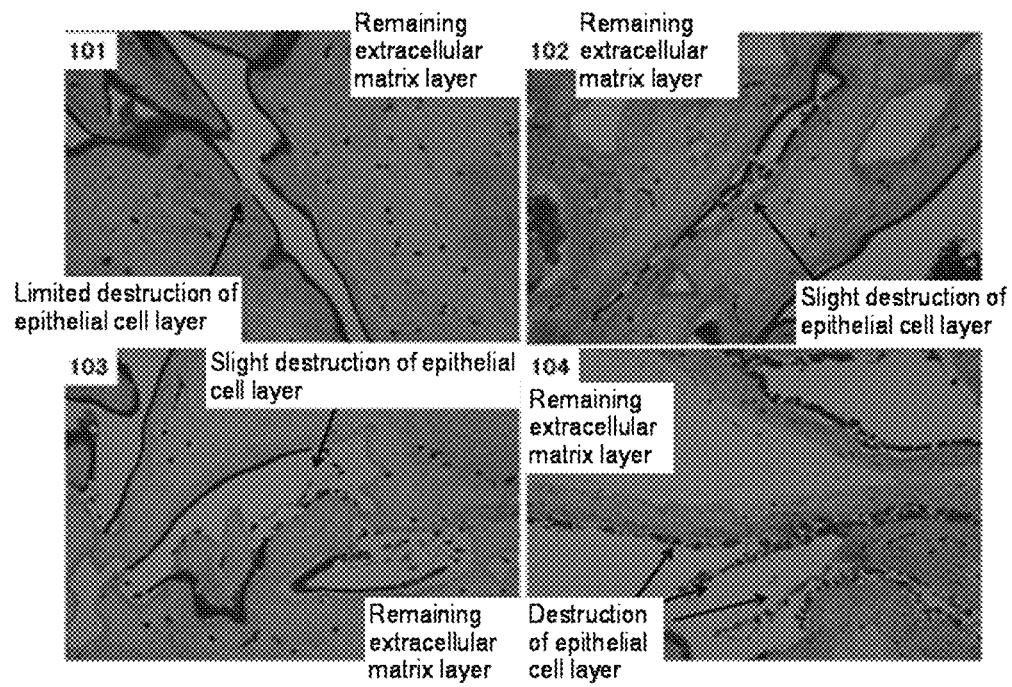

[Fig. 15]
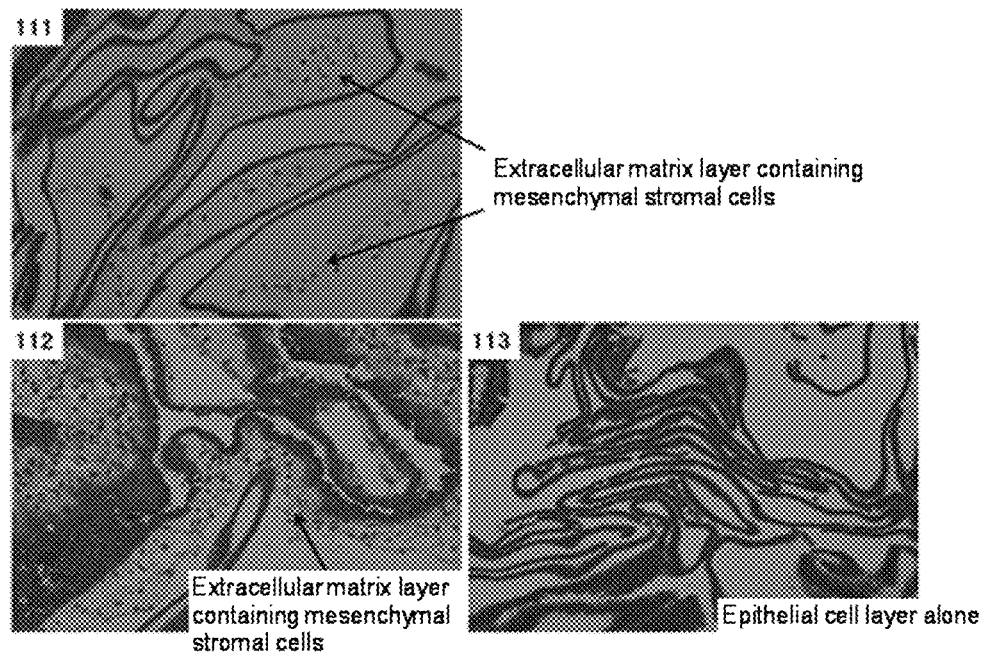
[Fig. 16]
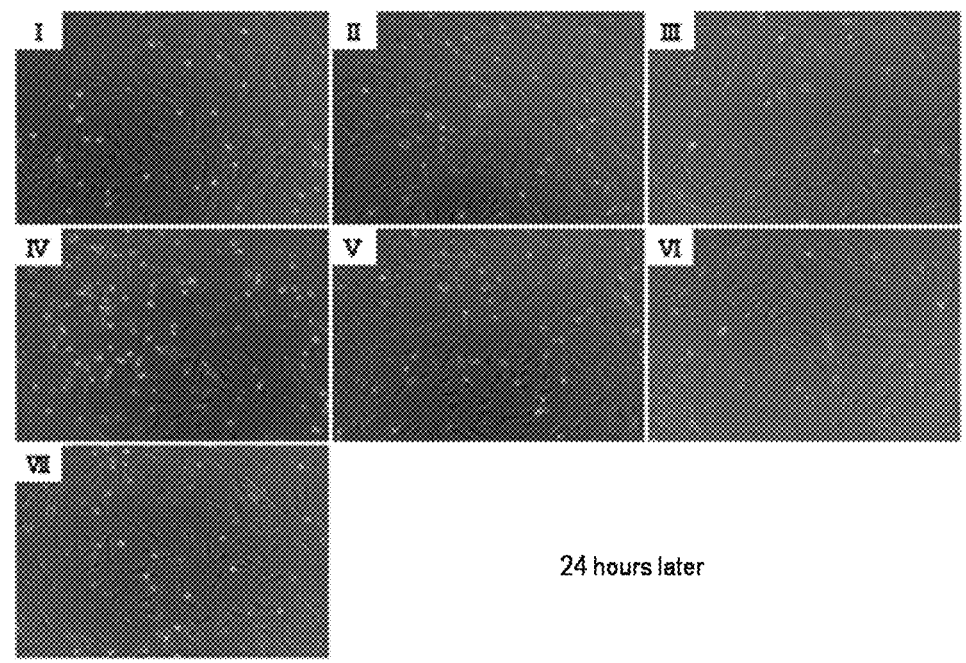
24 hours later

[Fig. 17]
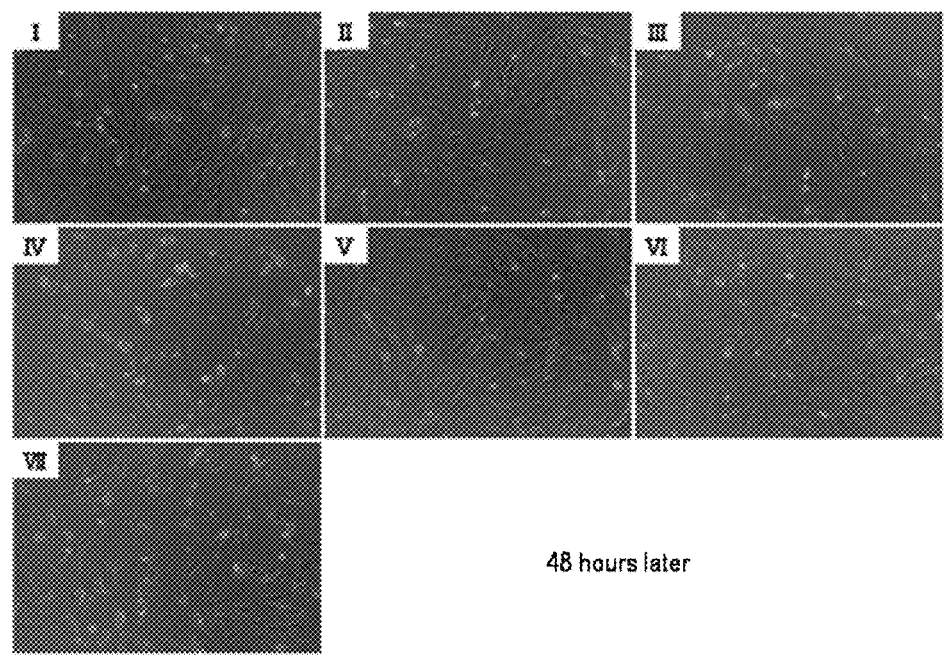
48 hours later
[Fig. 18]
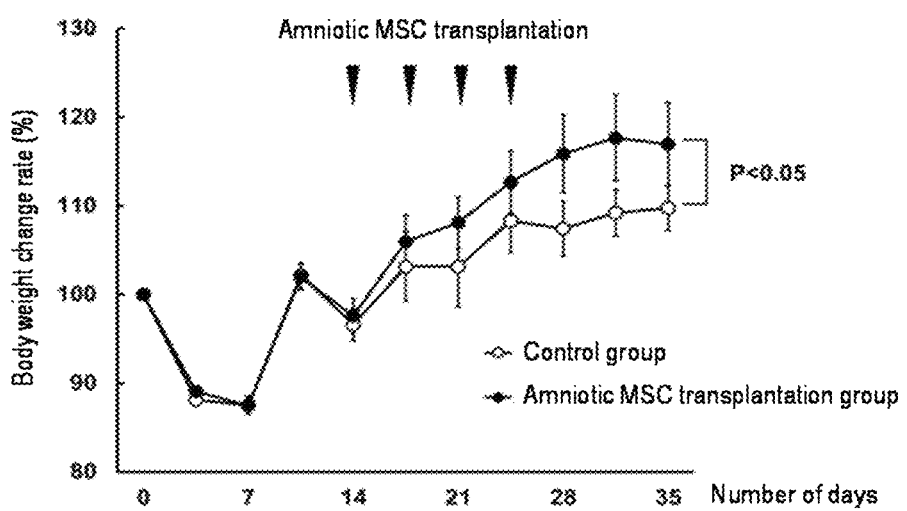

[Fig. 19]
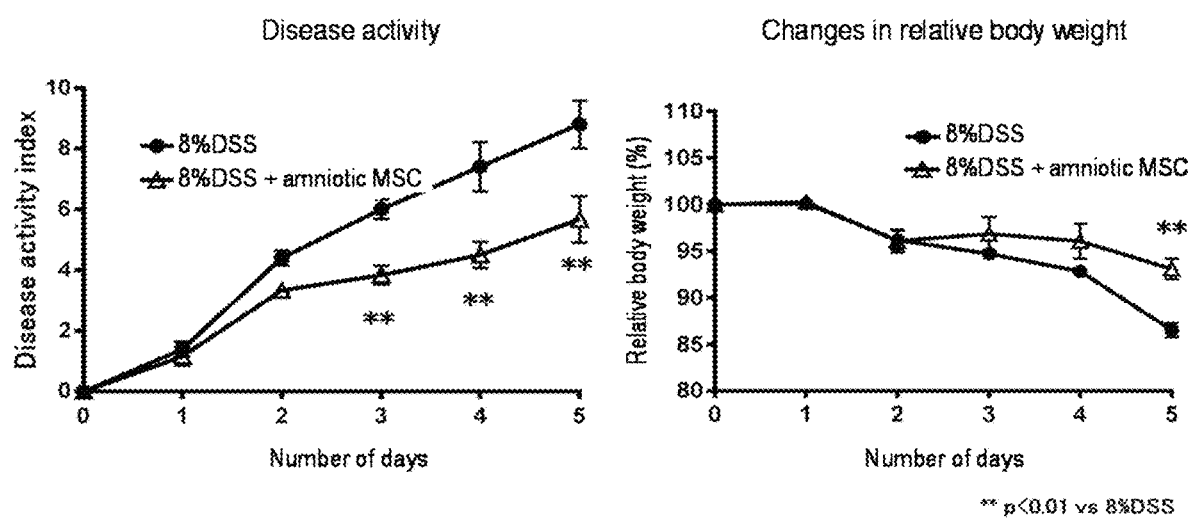
[Fig. 20]
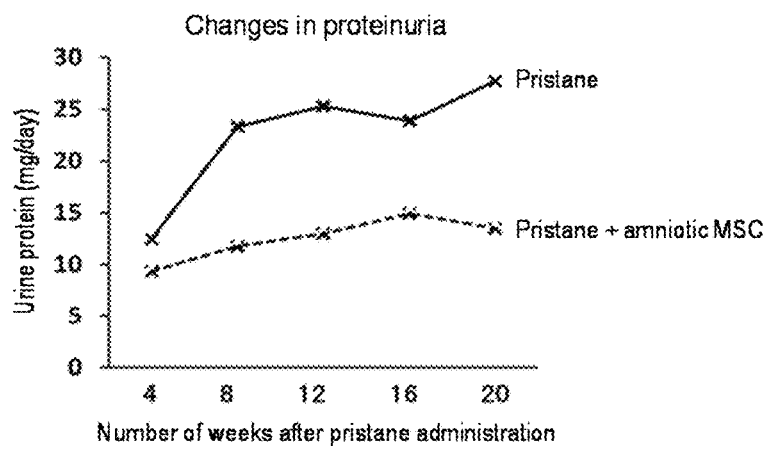

[Fig. 21]
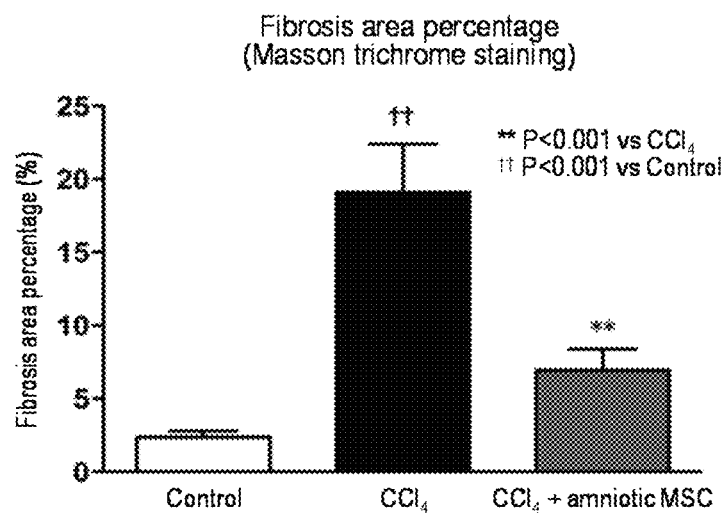
[Fig. 22]
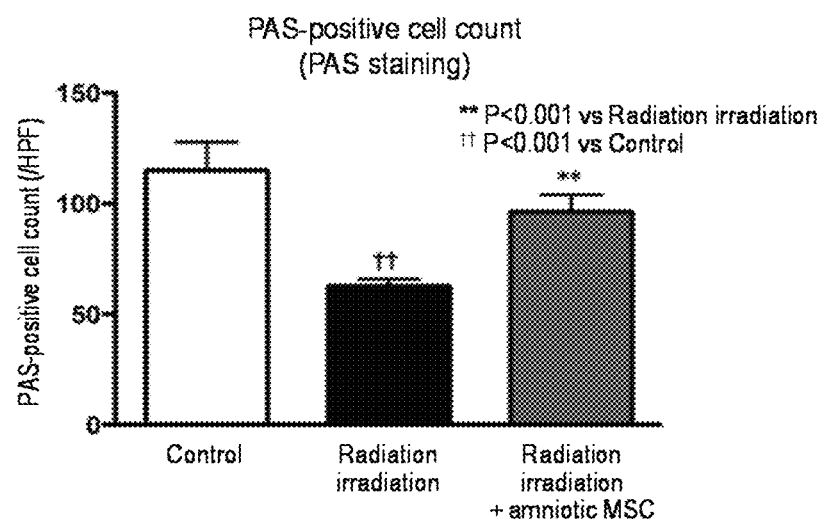

METHOD FOR PRODUCING AMNIOTIC MESENCHYMAL STROMAL CELL COMPOSITION, METHOD FOR CRYOPRESERVING THE SAME, AND THERAPEUTIC AGENT

CROSS REFERENCES TO RELATED APPLICATIONS

This application is a continuation of U.S. patent application Ser. No. 14/912,662, filed Feb. 18, 2016, which is a National Stage of International Application No. PCT/JP2014/071546, filed Aug. 18, 2014, the disclosures of which are incorporated herein by reference in their entireties. This application claims priority to Japanese Application No. 2014-130142, filed Jun. 25, 2014 and 2013-170008 filed Aug. 19, 2013.

TECHNICAL FIELD

The present invention relates to a method for producing a mesenchymal stromal cell composition, which comprises separating mesenchymal stromal cells (MSCs) that are suitable for applied use in cell therapy from an amnion with high purity in a convenient manner. The present invention further relates to a method for producing a cryopreserved mesenchymal stromal cell composition, and a therapeutic agent comprising the mesenchymal stromal cell composition.

BACKGROUND ART

Mesenchymal stem cells are somatic stem cells, which have been found to exist in the bone marrow. Mesenchymal stem cells used as stem cells are capable of differentiating into bones, cartilage, and fats. Mesenchymal stem cells have been gaining attention as a potential cell source in cell therapy. Recently, it has been revealed that they also exist in the fetal appendage including the placenta, umbilical cord, and fetal membrane.

At present, mesenchymal stem cells have been gaining attention because of immunosuppressive capacity as well as differentiation capacity. There are ongoing clinical studies on hematopoietic stem cell transplantation for acute graft-versus-host disease (GVHD) and Crohn's disease which is an inflammatory bowel disease with the use of bone-marrow-derived mesenchymal stem cells. The present inventors conducted studies with an aim of realizing the applied use of fetal appendage-derived mesenchymal stem cells for immune-related diseases in clinical practice. Previously, the present inventors reported that fetal appendage-derived mesenchymal stem cells have differentiation capacity similar to that of bone marrow-derived mesenchymal stem cells (Non-Patent Document 6), fetal-membrane-derived mesenchymal stem cells can improve pathological conditions of rat autoimmune myocarditis models (Non-Patent Document 7), and umbilical cord-derived mesenchymal stem cells can improve the life-saving rate of mouse acute graft-versus-host disease (GVHD) models (Non-Patent Document 8). With the use of fetal appendage-derived mesenchymal stem cells, a large number of mesenchymal stem cells can be obtained at once, mass culture can be performed within a short period of time at low cost, non-invasive cell collection is possible, and high immunosuppressive effects can be obtained, compared with bone marrow-derived mesenchymal stem cells (Non-Patent Document 7). In consideration of the above, since MSCs such as fetal appendage-derived mesenchymal stem cells have remarkable immunosuppressive effects, they are applicable for cell therapy of various immune-related diseases.

Hitherto, a method for obtaining human fetal-derived pluripotent stem cells from the fetal appendage including the fetal membrane, placenta, and amniotic fluid has been reported (Patent Document 1). Patent Document 1 discloses a method for separating such stem cells which are regarded as c-kit (CD117)-positive cells by flow cytometry. In addition, a method for obtaining stem cells/progenitor cells having capacity to differentiate into various adult and child cells from the placenta and umbilical cord has been reported (Patent Document 2). Patent Document 2 discloses a method for separating stem cells/progenitor cells having capacity to differentiate into cells that constitute various organs and tissues (=comparable or superior to differentiation capacity of mesenchymal stem cells) contained in the placenta and umbilical cord.

In general, degradative enzymes such as trypsin, collagenase and dispase have been used for separating cells including fetal-appendage-derived stem cells and progenitor cells (Patent Document 1 and 2 and Non-Patent Document 1 to 4). The fetal membrane included in the fetal appendage is divided into an amnion which is in contact with amniotic fluid and positioned closest to the fetus and a chorion which is positioned outside of the amnion. According to an ordinary method, fetal-membrane (amnion and chorion)-derived MSCs are also separated using degradative enzymes (Non-Patent Document 1 and 4).

The amnion which is a part of the fetal membrane of the fetal appendage is divided into the epithelial cell layer which is in contact with amniotic fluid and the extracellular matrix layer containing MSCs which is positioned under the epithelial cell layer (FIG. 1). Therefore, if the amnion as a whole is treated with trypsin, not only the extracellular matrix layer but also the basal membrane that supports the epithelial cell layer are digested, which results in a mixture of epithelial cells and MSCs. This has been problematic. In order to solve this problem, for example, Non-Patent Document 1 to 3 disclose methods for recovering MSCs, comprising removing epithelial cells in advance using a degradative enzyme or by a manual technique to separate high-purity MSCs from the amnion and treating the remaining extracellular matrix layer again with a separation enzyme. However, according to these methods, epithelial cells cannot be completely removed or the recovery amount of MSC decreases, which has been problematic.

Further, in order to realize the on-demand use of fetal membrane MSCs for cell therapy, cryopreservation is essential. At a research level, a variety of cells cryopreservation solutions containing dimethylsulfoxide (DMSO) as a base component have been commercially available. Also, a cryopreservation solution containing 10% DMSO has been used in clinical studies of bone marrow MSCs. However, DMSO-based cryopreservation solutions cause reduction of the cell survival rate after thawing, which has been problematic.

PRIOR ART DOCUMENTS

Patent Documents

Patent Document 1: JP Patent No. 4330995
Patent Document 2: JP Patent No. 3934539
Patent Document 3: JP 2010-518096 A Non-Patent Documents Non-Patent Document 1: Am J Obstet Gynecol. 2004; 190 (1): 87-92
Non-Patent Document 2: Am J Obstet Gynecol. 2006; 194 (3): 664-73
Non-Patent Document 3: Current Protocols in Stem Cell Biology 1E.5
Non-Patent Document 4: J Tissue Eng Regen Med. 2007; 1 (4): 296-305
Non-Patent Document 5: Cytotherapy. 2006; 8 (4): 315-7
Non-Patent Document 6: Stem Cells. 2008; 26 (10): 2625-33
Non-Patent Document 7: J Mol Cell Cardiol. 2012; 53 (3): 420-8
Non-Patent Document 8: Cytotherapy. 2012; 14 (4): 441-50
Non-Patent Document 9: BMC Biotechnology 2012; 12: 49

SUMMARY OF INVENTION

Object to be Solved by the Invention

In consideration of cell formulation of human amnion-derived MSCs, it is preferable that production steps be as simple as possible in order to avoid contamination with bacteria/viruses and the like. A plurality of times of enzyme treatment requires the removal of enzymes via washing/centrifugation over the course of enzyme treatment, which results in reduction of the MSC recovery efficiency. In addition, according to known methods, epithelial cells are not completely removed in steps using degradative enzymes (Non-Patent Document 3 and Example 3) and therefore many epithelial cells remain adherent to the amnion.

In addition, it is desirable to minimize the concentration of a cell preservation solution because DMSO has cytotoxicity. There is also a report on a cryopreservation solution for which the DMSO content has been reduced using rat bone-marrow-derived MSCs (Non-Patent Document 9).

The present invention has been made in view of the above problems. An object of the present invention is to provide a method for producing a mesenchymal stromal cell composition, comprising conveniently and aseptically separating high-purity amnion-derived MSCs by performing enzyme treatment only once. Further, another object of the present invention is to provide a method for producing cryopreserved mesenchymal stromal cells which are prevented from aggregating and optimized for MSC transplantation. Moreover, another object of the present invention is to provide a cell therapy agent comprising amnion-derived MSCs produced by the above method.

Means for Solving the Object

As a result of intensive studies in order to achieve the above objects, the present inventors found that mesenchymal stromal cells can be separated with high purity by subjecting an amnion to enzyme treatment with collagenase and thermolysin and/or dispase and filtering the enzyme-treated amnion through a mesh. Further, the present inventors found that a mixture of mesenchymal stromal cells and a solution containing dimethylsulfoxide at a content of 5% to 10% by mass and hydroxyethyl starch at a content of 5% to 10% by mass or dextran at a content of 1% to 5% by mass is cryopreserved such that cryopreserved mesenchymal stromal cells optimized for MSC transplantation can be produced. Furthermore, the present inventors demonstrated that a mesenchymal stromal cell composition obtained by the above method is useful as a cell therapy agent. These findings have led to the completion of the present invention.

Specifically, according to the present invention, the following are provided.

(1) A method for producing a mesenchymal stromal cell composition, comprising: performing enzyme treatment of an amnion with collagenase and thermolysin and/or dispase; and filtering the enzyme-treated amnion through a mesh.
(2) The method for producing a mesenchymal stromal cell composition according to (1), further comprising recovering cells that have passed through the mesh; and culturing the recovered cells.
(3) The method for producing a mesenchymal stromal cell composition according to (2), wherein recovering cells that have passed through the mesh is diluting a filtrate with at least two times its volume of a medium or balanced salt solution and recovering mesenchymal stromal cells by centrifugation.
(4) The method for producing a mesenchymal stromal cell composition according to any one of (1) to (3), wherein the collagenase concentration is 50 CDU/ml to 1000 CDU/ml, and the thermolysin and/or dispase concentration is 100 PU/ml to 800 PU/ml
(5) The method for producing a mesenchymal stromal cell composition according to any one of (1) to (4), wherein performing enzyme treatment is performing the treatment at 30° C. to 40° C. for 30 minutes or more.
(6) The method for producing a mesenchymal stromal cell composition according to any one of (1) to (5), wherein performing enzyme treatment is stirring using a stirrer or shaker at 10 rpm/minute to 100 rpm/minute for 30 minutes or more.
(7) The method for producing a mesenchymal stromal cell composition according to any one of (1) to (6), wherein the amnion is obtained by Caesarean section.
(8) The method for producing a mesenchymal stromal cell composition according to any one of (1) to (7), wherein the pore size of the mesh is 40 to 200 μm.
(9) The method for producing a mesenchymal stromal cell composition according to any one of (1) to (8), wherein filtering the enzyme-treated amnion through a mesh involves use of free fall.
(10) A mesenchymal stromal cell composition, comprising CD324- and CD326-positive epithelial cells at a content of 20% or less and CD90-positive cells at a content of 75% or more, wherein the viable cell rate is 80% or more.
(11) The mesenchymal stromal cell composition according (10), which is obtained by the method for producing a mesenchymal stromal cell composition according to any one of (1) to (9).
(12) A mesenchymal stromal cell culture composition, which is obtained by culturing the mesenchymal stromal cell composition according to (10) or (11) in a medium containing albumin at a content of more than 0.05% by mass but not more than 5% by mass.
(13) A method for producing cryopreserved mesenchymal stromal cells, comprising cryopreserving a mixture of mesenchymal stromal cells and a solution containing dimethylsulfoxide at a content of 5% to 10% by mass and hydroxyethyl starch at a content of 5% to 10% by mass or dextran at a content of 1% to 5% by mass.
(14) The method for producing cryopreserved mesenchymal stromal cells according to (13), wherein the solution further contains human albumin at a content of more than 0% by mass but not more than 5% by mass.
(15) The method for producing cryopreserved mesenchymal stromal cells according to (13) or (14), wherein the mesenchymal stromal cells are mesenchymal stromal cells contained in a mesenchymal stromal cell composition produced by the method according to any one of (1)

to (9), mesenchymal stromal cells contained in the mesenchymal stromal cell composition according to (10) or (11), or mesenchymal stromal cells contained in the mesenchymal stromal cell culture composition according to (12).

(16) A method for producing a composition for mesenchymal stromal cell administration, comprising thawing cryopreserved mesenchymal stromal cells obtained by the method according to any one of (13) to (15) and diluting the cells two-fold or more with an infusion preparation.

(17) A cell therapy agent, comprising as an active ingredient the mesenchymal stromal cell composition according to (10) or (11), the mesenchymal stromal cell culture composition according to (12), and/or a composition for mesenchymal stromal cell administration produced by the method according to (16).

(18) The cell therapy agent according to (17), which is an injection preparation.

(19) The cell therapy agent according to (17), which is a preparation for transplantation having a cell aggregate or sheet-like structure.

(20) The cell therapy agent according to any one of (17) to (19), which is a therapeutic agent for a disease selected from graft-versus-host disease, inflammatory bowel disease, systemic lupus erythematosus, liver cirrhosis, or radiation enteritis.

(21) A method for treating a disease, comprising administering the mesenchymal stromal cell composition according to (10) or (11), the mesenchymal stromal cell culture composition according to (12), and/or a composition for mesenchymal stromal cell administration produced by the method according to (16) to a subject in need of cell therapy.

(22) The treatment method according to (21), wherein the composition is an injection preparation.

(23) The treatment method according to (21), wherein the composition is a preparation for transplantation having a cell aggregate or sheet-like structure.

(24) The treatment method according to any one of (21) to (23), wherein the disease is selected from graft-versus-host disease, inflammatory bowel disease, systemic lupus erythematosus, liver cirrhosis, or radiation enteritis.

Advantageous Effects of Invention

According to the present invention, human amnion-derived MSCs can be easily separated with good accuracy. Therefore, the present invention can be expected to promote industrial use of MSCs which have been confirmed to have efficacy in the field of regenerative medicine.

BRIEF DESCRIPTION OF DRAWINGS

FIG. 1 shows human amniotic tissue.

FIG. 2 explains the outline of an amnion-derived MSC separation method used in embodiments of the present invention.

FIG. 3 shows results of surface antigen marker expression analysis for cells obtained through enzyme treatment of a human amnion in which the collagenase concentration was maintained at a constant level and the thermolysin concentration was changed.

FIG. 4 shows HE staining images of tissue remaining on a filter after enzyme treatment of a human amnion in which the collagenase concentration was maintained at a constant level and the thermolysin concentration was changed.

FIG. 5 shows results of surface antigen marker expression analysis for cells obtained through enzyme treatment of a human amnion in which no collagenase was used and the thermolysin concentration was changed.

FIG. 6 shows HE staining images of tissue remaining on a filter after enzyme treatment of a human amnion in which no collagenase was used and the thermolysin concentration was changed.

FIG. 7 shows results of surface antigen marker expression analysis for cells obtained through enzyme treatment of a human amnion with the use of trypsin.

FIG. 8 shows HE staining images of tissue remaining on a filter after enzyme treatment of a human amnion with the use of trypsin.

FIG. 9 shows HE staining images of tissue remaining on a filter after enzyme treatment of a human amnion in which the thermolysin concentration was fixed to 250 PU/ml and the collagenase concentration was adjusted to different levels.

FIG. 10 shows HE staining images of tissue remaining on a filter after enzyme treatment of a human amnion in which the thermolysin concentration was fixed to 500 PU/ml and the collagenase concentration was adjusted to different levels.

FIG. 11 shows results of surface antigen marker expression analysis for cells obtained through enzyme treatment of a human amnion in which the collagenase concentration was maintained at a constant level and the dispase concentration was changed.

FIG. 12 shows HE staining images of tissue remaining on a filter after enzyme treatment of a human amnion in which the collagenase concentration was maintained at a constant level and the dispase concentration was changed.

FIG. 13 shows results of surface antigen marker expression analysis for cells obtained through enzyme treatment of a human amnion in which no collagenase was used and the dispase concentration was changed.

FIG. 14 shows HE staining images of tissue remaining on a filter after enzyme treatment of a human amnion in which no collagenase was used and the dispase concentration was changed.

FIG. 15 shows HE staining images of tissue remaining on a filter after enzyme treatment of a human amnion in which the dispase concentration was fixed to 250 PU/ml and the collagenase concentration was adjusted to different levels.

FIG. 16 shows photos taken 24 hours after seeding amnion-derived MSCs contained in rapidly thawed cryopreservation solutions in wells of a plastic plate.

FIG. 17 shows photos taken 48 hours after seeding amnion-derived MSCs contained in rapidly thawed cryopreservation solutions in wells of a plastic plate.

FIG. 18 shows time-dependent changes in the body weight change rate, which indicate therapeutic effects of amnion-derived MSC transplantation in mouse acute GVHD models.

FIG. 19 shows time-dependent changes in disease activity and large bowel lengths on day 5 of treatment, which indicate therapeutic effects of amnion-derived MSC transplantation in rat inflammatory bowel disease models.

FIG. 20 shows time-dependent changes in urine protein, which indicate therapeutic effects of amnion-derived MSC transplantation in mouse systemic lupus erythematosus models.

FIG. 21 is a graph of the liver fibrosis area percentage, which indicates therapeutic effects of amnion-derived MSC transplantation in rat liver cirrhosis models.

FIG. 22 is a graph of the PAS-positive goblet cell count obtained through rectal PAS staining, which indicates therapeutic effects of amnion-derived MSC transplantation in rat radiation enteritis models.

EMBODIMENT OF CARRYING OUT THE INVENTION

Embodiments of the present invention are specifically explained below with reference to the drawings. However, these embodiments are intended to facilitate understanding of the principles of the present invention, and therefore, the scope of the present invention is not limited to the embodiments. The present invention encompasses other embodiments with appropriate modifications made by a person skilled in the art.

[1] Explanation of Terms

The term "fetal appendage" used herein refers to a fetal membrane, a placenta, an umbilical cord, and amniotic fluid. In addition, the term "fetal membrane" refers to a fetal sac containing fetal amniotic fluid, which comprises an amnion, a chorion, and a decidua in that order from the inside. The amnion and chorion are originated from the fetus. The term "amnion" refers to a transparent thin membrane with few blood vessels, which is located in the most inner layer of the fetal membrane. The inner wall of the amnion is covered with a layer of epithelial cells having a secretory function and secretes amniotic fluid.

The term "mesenchymal stromal cell (MSC)" used herein refers to cells that include mesenchymal cells and progenitor cells (cells having capacity to differentiate into cells that constitute one or more of various organs and tissues), which satisfy the definition of "pluripotent mesenchymal stromal cell (MSC)" proposed by the International Society for Cellular Therapy (see Non-Patent Document 5 and the descriptions below).

Definition of Pluripotent Mesenchymal Stromal Cells
i) Adherence to plastic in standard medium under culture conditions
ii) Specific surface antigen expression (positive for CD105, CD73, and CD90, and negative for CD45, CD34, CD14, CD11b, CD79 alpha, CD19, and HLA-DR)
iii) Differentiation potential into osteocytes, fat cells and chondrocytes under culture conditions The term "mesenchymal stromal cell composition" used herein refers to any composition containing mesenchymal stromal cells. Examples thereof include, but are not particularly limited to, a cell suspension containing mesenchymal stromal cells obtained after treatment of an amnion with a degradative enzyme.

The term "mesenchymal stromal cell culture composition" used herein refers to, for example, a cell suspension obtained by culturing the mesenchymal stromal cell composition.

The term "composition for mesenchymal stromal cell administration" used herein refers to any composition that was prepared in a form which is appropriate for administration by using the above mesenchymal stromal cell composition. Examples thereof include, but are not particularly limited to, a cell suspension obtained by adding an infusion preparation to a mixture of mesenchymal stromal cells and a solution containing dimethylsulfoxide at a content of 5% to 10% by mass and hydroxyethyl starch at a content of 5% to 10% by mass or dextran at a content of 1% to 5% by mass, wherein the volume of the infusion preparation is two times or more the volume of the mixture.

[2] Method for Producing a Mesenchymal Stromal Cell Composition

The method for producing a mesenchymal stromal cell composition of the present invention comprises performing enzyme treatment of an amnion with collagenase and thermolysin and/or dispase; and filtering the enzyme-treated amnion through a mesh.

In one example of the method for producing a mesenchymal stromal cell composition of the present invention, it is possible to treat a human amnion only once in an enzyme liquid containing collagenase and thermolysin and/or dispase at the adjusted optimum concentrations and filter the enzyme-treated solution containing the digested amnion through a mesh. An epithelial cell layer containing a basal membrane that is not digested with collagenase and thermolysin and/or dispase at the adjusted optimum concentrations remains on the mesh while MSCs contained in an extracellular matrix layer that is digested with collagenase and thermolysin and/or dispase at the adjusted optimum concentrations pass through the mesh. It is therefore possible to recover MSCs by collecting cells that have passed through the mesh. Further, it is also possible to produce a mesenchymal stromal cell composition by culturing the recovered cells.

FIG. 1 shows human amniotic tissue. As shown in FIG. 1, an amnion comprises an epithelial cell layer serving as a surface layer and an extracellular matrix layer that exists under the epithelial cell layer. The extracellular matrix layer contains MSCs. Like other epithelial cells, amniotic epithelial cells are characterized in that they express epithelial cadherin (E-cadherin: CD324) and an epithelial cell adhesion factor (EpCAM: CD326) while MSCs do not express such epithelial-specific surface antigen markers. Thus, they can be easily distinguished by FACS (FIG. 3).

FIG. 2 explains the outline of an amnion-derived MSC separation method used in the embodiments of the present invention. An amnion is collected from the human fetal appendage in a physical manner (A). The amnion is washed with an isotonic solution such as physiological saline (B). The amnion is immersed in a solution containing enzymes such as collagenase and thermolysin and/or dispase at the adjusted optimum concentrations during stirring and shaking at an appropriate temperature (C). As the epithelial cell layer structure is maintained because enzyme treatment targeting the extracellular matrix alone does not cause cells in the epithelial cell layer to be separated, the obtained solution of the digested amnion is filtered through a mesh (D). The epithelial cell layer is left on the mesh and MSCs contained in the extracellular matrix layer pass through the mesh, thereby allowing the cells to be recovered. Photo E shows centrifuge tubes, Photo F shows culture dishes, and Photo G shows culture cells.

One embodiment of the present invention is described in detail below.

1. A sample of the human fetal appendage of an elective Caesarean section case is aseptically obtained in an operating room.
2. An amnion is manually and aseptically removed from the fetal appendage.
3. The amnion is transferred to a sterile container (disposable cup) and washed with an isotonic solution such as physiological saline several times to remove adhering blood and the like.
4. The amnion is cut into several pieces with a scalpel/scissors or the like (this step may be omitted). The amnion may be preserved in medium at 2° C. to 8° C. for 24 to 48 hours before use.

5. The amnion is immersed in a solution containing collagenase and thermolysin and/or dispase at the adjusted optimum concentrations and then stirred and shaken at 37° C. and 60 rpm for 90 minutes using a thermostatic shaker.
6. Accordingly, the epithelial cell layer remains as a single layer and MSCs contained in the extracellular matrix layer are suspended in the enzyme-containing solution.
7. A Falcon cell strainer (100 μm mesh) is set to a sterile tube (50 ml Falcon tube) to filter the solution containing the cells after amnion digestion in a free fall motion, thereby allowing the epithelial cell layer to be left on the mesh and allowing only MSCs to pass through the mesh.
8. The solution containing MSCs that have passed through the mesh is diluted with a Hank's balanced salt solution, and then mesenchymal stromal cells are formed into a pellet by centrifugation at 400×g for 5 minutes.
9. The pellet is diluted with αMEM supplemented with 10% FBS, followed by seeding in a plastic flask for culture.

According to the present invention, it is possible to prevent reduction of the cell recovery rate and contamination with microorganisms, etc due to enzyme treatment that is performed multiple times with centrifugation and washing after each enzyme treatment in conventional methods. It is also possible to prepare a large amount of uniform MSCs in a convenient manner within a short period of time without a purification operation involving, for example, Ficoll density gradient centrifugation.

A combination of enzymes used for separation of amnion-derived MSCs in the present invention includes collagenase that exclusively digests collagen and thermolysin and/or dispase used as a metalloproteinase that cleaves the N-terminal end of a non-polar amino acid.

According to the present invention, a combination of collagenase and thermolysin and/or dispase is used. Alternatively, an enzyme that separates MSCs but does not decompose the epithelial cell layer (or a combination including such enzyme) also can be used. A preferable combination of the concentrations of collagenase and thermolysin and/or dispase can be determined by microscopic observation after enzyme treatment or FACS. Preferable concentration conditions allow the epithelial cell layer not to be decomposed and MSCs contained in the extracellular matrix layer to be separated.

The collagenase concentration is preferably 50 CDU/ml to 1000 CDU/ml, and the thermolysin and/or dispase concentration is preferably 100 PU/ml to 800 PU/ml.

In the case of treatment with collagenase (300 CDU/ml) alone, the viable cell count was $0.29 \times 10^6$ cells. When thermolysin was added, the viable cell count increased in a concentration-dependent manner. When the thermolysin concentration was 400 PU/ml, the viable cell count was increased to $1.99 \times 10^6$ cells, which was about 7 times the above cell count, and the viable cell rate was found to be 91.7% (Example 1, Table 1).

Similarly, when dispase was added to collagenase (300 CDU/ml), the viable cell count increased in a concentration-dependent manner. When the dispase concentration was 200 PU/ml, the viable cell count increased to $3.02 \times 10^6$ cells, and the viable cell rate was found to be 83.7% (Example 6, Table 8). Therefore, an increased number of viable cells can be obtained by simultaneous enzyme treatment with collagenase and thermolysin or dispase but not collagenase alone.

When the collagenase concentration was 300 CDU/ml, the optimum thermolysin concentration was found to be 400 PU/ml. In this case, the CD90-positive MSC content was 83.3%, and the CD324-positive epithelial cell content was 12.8% (Example 1, Table 2). In addition, when the collagenase was 300 CDU/ml, the optimum concentration of dispase to be added was found to be 200 PU/ml. In this case, the CD90-positive MSC content was 83.3%, and the CD324-positive epithelial cell content was 12.8% (Example 6, Table 9).

When thermolysin and dispase alone were added at concentrations of more than 400 PU/ml, a phenomenon of epithelial cell destruction was observed (Example 2, FIG. 6, Example 7, and FIG. 14).

When the collagenase concentration was 300 CDU/ml and the thermolysin concentration was 250 PU/ml, the CD90-positive MSC content was 93.3% and the CD90-positive MSC cell count was $1.43 \times 10^6$ cells (Example 4, Table 6). In addition, when the collagenase concentration was 300 CDU/ml and the dispase concentration was 250 PU/ml, the CD90-positive MSC content was 91.5% and the CD90-positive MSC cell count was $1.49 \times 10^6$ cells (Example 8, Table 11).

It is preferable that enzyme treatment be performed by immersing an amnion washed with physiological saline or the like in an enzyme liquid, followed by treatment during stirring with the use of a stirrer or shaker. Alternatively, different stirring means can be used as long as MSCs can be separated with good efficiency. Accordingly, MSCs contained in the extracellular matrix layer can be separated. Preferably, enzyme treatment can be performed by stirring with the use of a stirrer or shaker at 10 rpm/minute to 100 rpm/minute for 30 minutes or more. In addition, the upper limit of enzyme treatment time is not particularly limited. However, enzyme treatment can be performed within generally 6 hours or less and preferably 3 hours or less, for example, 90 minutes or less. In addition, the enzyme treatment temperature is not particularly limited as long as the object of the present invention can be achieved. It is preferably 30° C. to 40° C. and more preferably 30° C. to 37° C.

In the above case, it is important to set a combination of the concentrations that does not cause the epithelial cell layer to be decomposed. This is because incorporation of epithelial cells causes a relative decrease in the MSC content.

As a result of filtration of an enzyme solution containing separated MSCs through a mesh, only the separated cells pass through the mesh such that the non-decomposed epithelial cell layer cannot pass through the mesh and thus it is left on the mesh. Thus, the separated MSCs can be easily recovered. In this case, the pore size of the mesh is not particularly limited as long as the object of the present invention can be achieved. However, it is preferably 40 to 200 μm, more preferably 40 to 150 μm, further preferably 70 to 150 μm, and particularly preferably 100 to 150 μm. When the pore size of the mesh is set within the above range, cells fall in a free fall motion without pressurization, thereby preventing reduction of the cell survival rate.

Regarding mesh material, a nylon mesh is preferably used. A tube having a 40 μm, 70 μm, or 100 μm nylon mesh such as a Falcon cell strainer that is widely used for research purposes is available. Alternatively, medical mesh cloth (nylon and polyester) used for hemodialysis and the like is available. Further, an arterial filter used for extracorporeal circulation (polyester mesh; 40 μm to 120 μm) is also available. A mesh made of other material such as a stainless-steel mesh (wire mesh) also can be used.

Preferably, MSCs are allowed to pass through a mesh in a free fall motion. It is also possible to force the cells to pass through a mesh by suction using a pump or the like. In this case, in order to avoid damage of cells, minimum necessary pressurization is desirable.

MSCs that have passed through a mesh are diluted with two times or more its volume of a medium or balanced salt buffer solution. Thereafter, MSCs can be recovered by centrifugation. A mesenchymal stromal cell culture composition can be produced with the recovered cells, if desired, after culture for cell proliferation. The medium used herein is αMEM/M199 with an albumin content of more than 0.05% but not more than 5% or a medium comprising such αMEM/M199 as a basal medium. Note that proliferative capacity declines in DMEM/F12/RPMI1640 or a medium comprising DMEM/F12/RPMI1640 as a basal medium. A desirable medium is αMEM medium containing a bovine/human serum content of 10% or more. Culture is performed in a plastic dish/flask in a 5% $CO_2$ environment at 37° C. Examples of a balanced salt buffer solution that can be used include buffered solutions such as Dulbecco's phosphate-buffered saline (DPBS), Earle's balanced salt solution (EBSS), Hank's balanced salt solution (HBSS), and phosphate-buffered saline (PBS).

According to the method of the present invention described above, it is possible to produce a mesenchymal stromal cell composition, which is characterized in that the CD324- and CD326-positive epithelial cell content is 20% or less, the CD90-positive cell content is 75% or more, and the viable cell rate is 80% or more. The present invention also encompasses such mesenchymal stromal cell composition.

[3] Method for Producing Cryopreserved Mesenchymal Stromal Cells

The method for producing cryopreserved mesenchymal stromal cells according to the present invention comprises cryopreserving a mixture comprising mesenchymal stromal cells and a solution containing dimethylsulfoxide at a content of 5% to 10% by mass and hydroxyethyl starch at a content of 5% to 10% by mass or dextran at a content of 1% to 5% by mass.

As a result of intensive studies, the present inventors found that the MSC survival rate decreases after thawing, which is probably because of cytotoxicity of high-concentration DMSO (Examples). It has been revealed that it is preferable to reduce the DMSO content in a cryopreservation solution used as a cryopreservation solution of human MSCs for cell transplantation from the standpoint of suppression of cell death. An MSC cryopreservation solution used in the method of the present invention is characterized in that the DMSO content is reduced and hydroxyethyl starch (HES) or dextran (e.g., Dextran 40) is added instead of DMSO. Such cryopreservation solution may further comprise human albumin at a content of more than 0% by mass but not more than 5% by mass. One example of such cryopreservation solution that can be used is a cryopreservation solution having a composition comprising DMSO (5% by mass), HES (6% by mass), and human albumin (4% by mass).

Cryopreserved mesenchymal stromal cells can be produced using the above cryopreservation solution and a program freezer by, for example, decreasing the temperature to a level of −30° C. to −50° C. (e.g., −40° C.) at a freezing rate of −1° C. to −2° C./minute and further decreasing the temperature to a level of −80° C. to −100° C. (e.g., −90° C.) at a freezing rate of −10° C./minute.

A composition for mesenchymal stromal cell administration can be produced by thawing the cryopreserved mesenchymal stromal cells obtained by the above method and diluting the cells two-fold or more with an infusion preparation.

[4] Cell Therapy Agent

MSCs (including proliferated MSCs) prepared above can be used for therapeutic agents for intractable diseases.

That is, according to the present invention, a cell therapy agent comprising as an active ingredient the above-mentioned mesenchymal stromal cell composition and/or mesenchymal stromal cell culture composition and/or composition for mesenchymal stromal cell administration can be provided. Further, according to the present invention, the mesenchymal stromal cell composition and/or mesenchymal stromal cell culture composition and/or composition for mesenchymal stromal cell administration used for cell transplantation therapy can be provided. Furthermore, according to the present invention, a method for transplanting cells to a subject and a method for treating a disease of a subject, which comprises administering a therapeutically effective amount of the mesenchymal stromal cell composition and/or mesenchymal stromal cell culture composition and/or composition for mesenchymal stromal cell administration to the subject, can be provided.

The cell therapy agent and the mesenchymal stromal cell composition and/or mesenchymal stromal cell culture composition and/or composition for mesenchymal stromal cell administration of the present invention can be applied to, for example, graft-versus-host disease (GVHD, Example 10), inflammatory bowel disease such as Crohn's disease (Example 11) or ulcerous colitis, connective tissue disease such as systemic lupus erythematosus (Example 12), liver cirrhosis (Example 13), radiation enteritis (Example 14), and atopic dermatitis. Inflammation can be suppressed by administering MSCs prepared by the production method of the present invention to a site to be treated at an amount at which efficacy can be determined.

It is necessary that, after rapid thawing, cryopreserved MSCs are used immediately after dilution with an infusion preparation such as physiological saline to maintain cell viability. This is because DMSO contained in a cryopreservation solution has cytotoxicity. Also, the above composition for mesenchymal stromal cell administration which has been diluted with an infusion preparation can be intravenously administered to a patient with graft-versus-host disease, inflammatory enteritis such as Crohn's disease, connective tissue disease such as systemic lupus erythematosus, liver cirrhosis, radiation enteritis, atopic dermatitis, or the like for treatment.

The "infusion preparation" used herein is not particularly limited as long as it is a solution used for treatment of humans. Examples thereof include physiological saline, 5% glucose solution, Ringer's solution, lactated Ringer's solution, acetated Ringer's solution, and Solutions I, II, III, and IV.

The method for administering a cell therapy agent of the present invention is not particularly limited. Examples of the form of administration include, but are not limited to, subcutaneous injection, intra-lymph nodal injection, intravenous injection, intraperitoneal injection, intrathoracic injection, direct localized injection, and direct localized transplantation.

Like bone marrow MSC preparations, the cell therapy agent of the present invention can be used as an injection preparation or a transplant preparation having a cell aggregate or sheet-like structure for treatment of other diseases.

The dose of the cell therapy agent of the present invention is determined based on the amount of cells that allows a subject to whom the agent has been administered to obtain therapeutic effects, compared with a subject to whom the agent has not been administered. A specific dose can be appropriately determined depending on the form of administration, route of administration, intended use, and subject's age, body weight, and symptoms, and the like. In one example, it corresponds to a mesenchymal stromal cell count of preferably $10^5$ to $10^9$ cells per kg body weight and more preferably $10^5$ to $10^8$ cells per kg body weight of a human (e.g., an adult) for single administration.

EXAMPLES

The present invention is specifically explained with reference to the Examples below; however, the present invention is not limited to the Examples.

Example 1

An amnion was manually separated from the human fetal appendage of a pregnant woman who was an elective Caesarean section case after the obtaining of informed consent. The amnion was washed twice with a Hank's balanced salt solution (free of Ca and Mg). A portion of the obtained amnion (1 g) was transferred to a container. A Hank's balanced salt solution (supplemented with Ca and Mg) containing purified collagenase (CLSPA, Worthington; Specification: >500 CDU/mg) at a concentration of 300 CDU/ml (=<600 µg/ml) and thermolysin (Wako Pure Chemical Industries, Ltd.; Specification: >7000 PU/mg) at a concentration of 0 to 400 PU/ml (=<60 µg/ml) (No. 1: 0 PU/ml; No. 2: 100 PU/ml; No. 3: 200 PU/ml; or No. 4: 400 PU/ml) (5 ml in total) was added thereto, followed by stirring and shaking with the use of a shaker at 37° C. and 60 rpm for 90 minutes. The obtained mixture was mixed with two times its volume of αMEM (Alpha Modification of Minimum Essential Medium Eagle) supplemented with 10% fetal bovine serum (FBS), followed by filtration through a nylon net filter (pore size: 100 µm). Tissue remaining on the filter was evaluated by hematoxylin-eosin (HE) staining. The filtrate was centrifuged at 400×g for 5 minutes. The supernatant was discarded. The resulting cells were resuspended in αMEM supplemented with 10% FB S. The cell count was obtained after trypan blue staining. The obtained cells were stained with a mesenchymal marker anti-CD90-FITC antibody and an epithelial marker anti-CD324-APC antibody (BD Bioscience) at 4° C. for 15 minutes. Then, 7-AAD dye was added to discriminate dead cells. Surface antigen marker analysis was carried out using a flow cytometer (FACSCanto; BD). Tables 1 and 2 and FIGS. 3 and 4 show the results.

CDU (=collagen digestion unit): Enzyme amount at which amino acids and peptides corresponding to 1 µmol of leucine are generated using collagen as a substrate at 37° C. and pH 7.5 for 5 hours.

PU (=protease unit): Enzyme amount at which amino acids and peptides corresponding to 1 µg of tyrosine are generated using lactic acid casein as a substrate, at 35° C. and pH 7.2 for 1 minute.

TABLE 1

| No. | collagenase (CDU/ml) | thermolysin (PU/ml) | Viable cells ($\times 10^6$ cells/g) | Dead cells ($\times 10^6$ cells/g) | Viable cell rate (%) |
|---|---|---|---|---|---|
| 1 | 300 | 0 | 0.29 | 0.07 | 81 |
| 2 | 300 | 100 | 0.76 | 0.15 | 83.9 |
| 3 | 300 | 200 | 1.12 | 0.18 | 86.1 |
| 4 | 300 | 400 | 1.99 | 0.18 | 91.7 |

As shown in Table 1, the trypan blue-negative viable cell count obtained with the use of collagenase alone (No. 1) was $0.29 \times 10^6$ cells. However, as a result of the addition of thermolysin, the viable cell count increased to $1.99 \times 10^6$ cells for 400 PU/ml thermolysin (No. 4), which was about 7 times that for collagenase alone. Meanwhile, there was no remarkable change in the trypan blue-positive dead cell count, and the obtained viable cell rate was 80% or more for each sample.

As shown in FIG. 3, the results of flow cytometry showed that in the case of the sample of collagenase alone (No. 1), the proportion of CD90-positive MSCs of interest was only 34.6%, the proportion of unnecessary CD324-positive epithelial cells was 8.6%, and the proportion of other cells which were probably erythrocytes was 56.8%. As in Table 1, as a result of the addition of thermolysin, the proportion of CD90-positive MSCs increased. In the case of 400 PU/ml thermolysin (No. 4), the proportion of CD90-positive MSCs was 83.3%, the proportion of CD324-positive epithelial cells was 12.8%, and the proportion of other cells was 3.9%.

TABLE 2

| No. | collagenase (CDU/ml) | thermolysin (PU/ml) | Viable cells ($\times 10^6$ cells/g) | CD90-positive MSC (%) | CD90-positive MSC ($\times 10^6$ cells/g) |
|---|---|---|---|---|---|
| 1 | 300 | 0 | 0.29 | 34.6 | 0.1 |
| 2 | 300 | 100 | 0.76 | 79.8 | 0.61 |
| 3 | 300 | 200 | 1.12 | 87.5 | 0.98 |
| 4 | 300 | 400 | 1.99 | 83.3 | 1.66 |

As shown in Table 2, the MSC count obtained for each sample was $0.1 \times 10^6$ cells for collagenase alone (No. 1). However, as a result of the addition of thermolysin, the MSC count increased to $1.66 \times 10^6$ cells for 400 PU/ml thermolysin (No. 4), which was about 16 times that for No. 1.

As shown in FIG. 4, each enzyme-treated tissue remaining on the filter was subjected to HE staining for study. In the case of collagenase alone (No. 1), the extracellular matrix layer structure was maintained, indicating insufficient digestion. As a result of the addition of thermolysin, the extracellular matrix layer was digested. In the case of 400 PU/ml thermolysin (No. 4), the extracellular matrix layer was completely digested.

These results of Example 1 revealed that the use of collagenase alone did not cause the amnion to be digested; however, the addition of thermolysin to collagenase allowed the amnion to be digested in a concentration-dependent manner, and complete digestion of the extracellular matrix layer containing MSCs was observed with the use of 400 PU/ml thermolysin.

Example 2

In view of Example 1, further study was conducted in the above manner except that thermolysin was used without collagenase.

Table 3 and FIGS. 5 and 6 show the results.

TABLE 3

| No. | thermolysin (PU/ml) | Viable cells (×10⁶ cells/g) | Dead cells (×10⁶ cells/g) | Viable cell rate (%) |
|---|---|---|---|---|
| 31 | 400 | 0.38 | 0.18 | 67.9 |
| 32 | 800 | 1.31 | 0.65 | 66.8 |
| 33 | 2000 | 1.32 | 0.5 | 72.5 |
| 34 | 4000 | 1.19 | 0.27 | 81.1 |

As shown Table 3, the cell count per 1 g of human amnion obtained after digestion with thermolysin alone increased in a thermolysin-concentration-dependent manner.

However, as shown in FIG. 5, the results of flow cytometry of cells contained in the enzyme treatment solution containing thermolysin alone revealed that substantially 100% of cells obtained at each concentration were CD324-positive epithelial cells, indicating that no CD90-positive MSCs of interest were obtained.

As shown in FIG. 6, as a result of study by HE staining of each enzyme-treated tissue remaining on the filter, it was found that the extracellular matrix layer containing MSCs was not digested at all, and destruction of the epithelial cell layer took place in a thermolysin-concentration-dependent manner.

These results of Example 2 revealed that no MSCs of interest are obtained with the use of thermolysin alone, and the epithelial cell layer is destroyed at a thermolysin concentration of 800 PU/ml or more.

Example 3

Further, the method of the present invention was compared with the conventional method using trypsin (Non-Patent Document 3). A human amnion (1 g) was placed in a container and treated as follows: No. 41) stirring and shaking (with the use of a shaker) at 37° C. and 60 rpm for 90 minutes with the addition of 5 ml of 0.05% trypsin (containing 0.53 mM EDTA); No. 42) stirring and shaking (with the use of a shaker) at 37° C. and 60 rpm for 90 minutes with the addition of 5 ml of 0.05% trypsin (containing 0.53 mM EDTA; Invitrogen) followed by stirring and shaking (with the use of a shaker) of tissue remaining after filtration through a nylon net filter (pore size: 100 μm) at 37° C. and 60 rpm for 90 minutes with a Hank's balanced salt solution (containing Ca and Mg) supplemented with purified collagenase (300 CDU/ml); and No. 43) stirring and shaking (with the use of a shaker) at 37° C. for 90 minutes with 5 ml of a Hank's balanced salt solution (containing Ca and Mg) supplemented with purified collagenase (300 CDU/ml)+thermolysin (250 PU/ml). Thereafter, the assay was carried out as in Example 1. Tables 4 and 5 and FIGS. 7 and 8 show the results.

As shown in Table 4, the largest cell count was obtained from the sample (No. 42) which had been subjected to trypsin treatment and then collagenase treatment of the remaining amnion.

However, as shown in FIG. 7, the results of flow cytometry of cells contained in each enzyme treatment solution revealed that substantially no CD90-positive MSCs of interest were obtained (0.6%) using trypsin alone (No. 41). In the case of two-stage treatment (No. 42) in which collagenase treatment had been additionally performed after trypsin treatment, CD90-positive cells of interest were obtained (32.6%); however, unnecessary CD324-positive epithelial cells were also contained (65.6%). In the case of single treatment with collagenase+thermolysin (No. 43), the proportion of CD90-positive MSCs was 90.3%, and the proportion of CD324-positive epithelial cells was 8.0%.

TABLE 4

| No. | | Viable cells (×10⁶ cells/g) | Dead cells (×10⁶ cells/g) | Viable cell rate (%) |
|---|---|---|---|---|
| 41 | 0.05% Trypsin | 2.3 | 0.5 | 82.1 |
| 42 | 0.05% Trypsin(T) + 300 CDU/ml Collagenase(C) | 18.8 (T: 2.3 + C: 16.5) | 1.2 (T: 0.5 + C: 0.7) | 94 |
| 43 | 300 CDU/ml Collagenase + 250 PU/ml Thermolysin | 3.6 | 0.72 | 83.3 |

As shown in FIG. 8, as a result of study by HE staining of each enzyme-treated tissue remaining on the filter, trypsin treatment alone (No. 41) resulted in formation of separate spherical epithelial cells, in addition to destruction of the basal membrane of the epithelial cell layer, while the extracellular matrix layer structure was maintained. As a result of collagenase treatment following trypsin treatment (No. 42), complete digestion of amnion was confirmed. In the case of treatment with a combination of collagenase+thermolysin (No. 43), the structure of the epithelial cell layer including the basal membrane was maintained, although the extracellular matrix layer was completely digested.

TABLE 5

| No. | | Viable cells (×10⁶ cells/g) | CD90-positive MSC (%) | CD90-positive MSC (×10⁶ cells/g) | CD324-positive epithelial cells (%) | CD324-positive epithelial cells (×10⁶ cells/g) |
|---|---|---|---|---|---|---|
| 51 | 0.05% Trypsin | 2.3 | 0.6 | 0.01 | 97.8 | 2.25 |
| 52 | 0.05% Trypsin(T) + 300 CDU/ml Collagenase(C) | 18.8 T: 2.3 C: 16.5 | T: 0.6 C: 32.6 | 5.39 T: 0.01 C: 5.38 | T: 97.8 C: 65.6 | 13.07 T: 2.25 C: 10.82 |
| 53 | 300 CDU/ml Collagenase + 250 PU/ml Thermolysin | 3.6 | 90.3 | 3.25 | 8 | 0.29 |

As shown in Table 5, it was found that substantially no MSCs were obtained from each sample in the case of treatment with trypsin alone (No. 51), the cell count significantly increased to 5.39×10⁶ cells in the case of collagenase treatment following trypsin treatment (No. 52), and the cell count was 3.25×10⁶ cells in the case of collective treatment with collagenase+thermolysin (No. 53). Meanwhile, regarding unnecessary CD324-positive epithelial cells, the obtained cell counts were 2.25×10⁶ cells and 13.07×10⁶ cells for treatment with trypsin alone (No. 51) and collective treatment with trypsin+collagenase (No. 52), respectively, which were greater than the corresponding cell counts of necessary MSCs. In the case of collective treatment with collagenase+thermolysin (No. 53), the cell count of unnecessary CD324-positive epithelial cells was 0.29×10⁶ cells, which was smaller than that of MSCs.

Based on the above, according to the conventional method, which comprises performing collagenase treatment after trypsin treatment, a large number of cells can be obtained, which is advantageous. However, the method is disadvantageous in that many epithelial cells are incorporated, the method must comprise separating cells by specific gravity centrifugation or the like in order to obtain high purity MSCs, and the method requires two-stage treatment including trypsin treatment and collagenase treatment, which is complicated. In particular, two-stage treatment is disadvantageous in that trypsin is inactivated by calcium (Ca) while collagenase has calcium requirement, which makes it impossible to simultaneously carry out trypsin treatment and collagenase treatment.

Example 4

In view of Examples 1 to 3, the minimum necessary collagenase concentration for separation of amniotic mesenchymal stromal cells was further studied at a fixed thermolysin concentration of 250 PU/ml. Table 6 and FIG. 9 show the results.

proportion of CD90-positive mesenchymal stromal cells was 90% or more for each sample.

As shown in FIG. 9, study was carried out by HE staining of each enzyme-treated tissue remaining on the filter. When the collagenase concentrations were 300 CDU/ml and 150 CDU/ml (No. 63 and No. 62, respectively), only the epithelial cell layer was observed. Meanwhile, when the collagenase concentration was 75 CDU/ml (No. 61), the extracellular matrix layer was slightly observed, indicating insufficient digestion.

These results of Example 4 revealed that when the thermolysin concentration is fixed to 250 PU/ml, it is necessary to adjust the collagenase concentration to preferably at least 75 CDU/ml or more and more preferably 150 CDU/ml or more for sufficient digestion of the extracellular matrix layer.

Example 5

Further, the minimum necessary collagenase concentration for separation of amniotic mesenchymal stromal cells was studied at a fixed thermolysin concentration of 500 PU/ml that was two times that in Example 3. Table 7 and FIG. 10 show the results.

TABLE 7

| No. | collagenas (CDU/ml) | thermolysin (PU/ml) | Viable cells (×10⁶ cells/g) | Dead cells (×10⁶ cells/g) | Viable cell rate (%) | CD90-positive MSC (%) |
| --- | --- | --- | --- | --- | --- | --- |
| 71 | 37.5 | 500 | 0.82 | 0.14 | 85.1 | 93.7 |
| 72 | 75 | 500 | 2.03 | 0.27 | 88.3 | 96.6 |
| 73 | 150 | 500 | 2.05 | 0.26 | 88.7 | 97.4 |

As shown in Table 7, the trypan blue-negative viable cell count obtained at a collagenase concentration of 150 CDU/ml (No. 73) was 2.05×10⁶ cells. Meanwhile, when the collagenase concentration was a quarter (¼) of the above concentration (37.5 CDU/ml (No. 71)), the viable cell count decreased to 0.82×10⁶ cells. There was no remarkable change in the trypan blue-positive dead cell count, and the obtained viable cell rate was 80% or more for each sample. In addition, the results of flow cytometry showed that the proportion of CD90-positive mesenchymal stromal cells was 90% or more for each sample.

As shown in FIG. 10, study was carried out by HE staining of each enzyme-treated tissue remaining on the filter. When the collagenase concentrations were 150 CDU/ml and 75 CDU/ml (No. 73 and No. 72, respectively), only

TABLE 6

| No. | collagenas (CDU/ml) | thermolysin (PU/ml) | Viable cells (×10⁶ cells/g) | Dead cells (×10⁶ cells/g) | Viable cell rate (%) | CD90-positive MSC (%) |
| --- | --- | --- | --- | --- | --- | --- |
| 61 | 75 | 250 | 1.16 | 0.23 | 83.5 | 90.8 |
| 62 | 150 | 250 | 1.73 | 0.17 | 91.1 | 97.8 |
| 63 | 300 | 250 | 1.53 | 0.1 | 93.9 | 93.3 |

As shown in Table 6, the trypan blue-negative viable cell count obtained at a collagenase concentration of 300 CDU/ml (No. 63) was 1.53×10⁶ cells. Meanwhile, when the collagenase concentration was a quarter (¼) of the above concentration (75 CDU/ml) (No. 61), the viable cell count decreased to 1.16×10⁶ cells. There was no remarkable change in the trypan blue-positive dead cell count, and the obtained viable cell rate was 80% or more for each sample. In addition, the results of flow cytometry showed that the the epithelial cell layer was observed. Meanwhile, when the collagenase concentration was 37.5 CDU/ml (No. 71), the extracellular matrix layer was obviously observed, indicating insufficient digestion.

These results of Example 5 revealed that when the thermolysin concentration is fixed to 500 PU/ml, it is necessary to adjust the collagenase concentration to preferably 37.5 CDU/ml or more and more preferably 75 CDU/ml or more for sufficient digestion of the extracellular matrix layer.

Example 6

Regarding Example 1, study was carried out in the above manner except that dispase, which is a metalloproteinase that cleaves the N-terminal end of a non-polar amino acid, was used instead of thermolysin, and collagenase was added.

An amnion was manually separated from the human fetal appendage of a pregnant woman after the obtaining of informed consent. The amnion was washed twice with a Hank's balanced salt solution (free of Ca and Mg). A portion of the obtained amnion (1 g) was transferred to a container. A Hank's balanced salt solution (supplemented with Ca and Mg) containing collagenase (Brightase-C, Nippi, Inc.; Specification: >200,000 CDU/vial) at a concentration of 300 CDU/ml and dispase I (Wako Pure Chemical Industries, Ltd.; Specification: 10000 to 13000 PU/vial) at a concentration of 0 to 400 PU/ml (No. 1: 0 PU/ml; No. 2: 100 PU/ml; No. 3: 200 PU/ml; or No. 4: 400 PU/ml) (5 ml in total) was added thereto, followed by stirring and shaking with the use of a shaker at 37° C. and 60 rpm for 90 minutes. The obtained mixture was mixed with two times its volume of αMEM (Alpha Modification of Minimum Essential Medium Eagle) supplemented with 10% fetal bovine serum (FBS), followed by filtration through a nylon net filter (pore size: 100 μm). Tissue remaining on the filter was evaluated by hematoxylin-eosin (HE) staining. The filtrate was centrifuged at 400×g for 5 minutes. The supernatant was discarded. The resulting cells were resuspended in αMEM supplemented with 10% FBS. The cell count was obtained after trypan blue staining. The obtained cells were stained with a mesenchymal marker anti-CD90-FITC antibody and an epithelial marker anti-CD324-APC antibody (BD Bioscience) at 4° C. for 15 minutes. Then, 7-AAD dye was added to discriminate dead cells. Surface antigen marker analysis was carried out using a flow cytometer (FACSCanto; BD). Tables 8 and 9 and FIGS. 11 and 12 show the results.

TABLE 8

| No. | collagenase (CDU/ml) | dispase (PU/ml) | Viable cells (×10$^6$ cells/g) | Dead cells (×10$^6$ cells/g) | Viable cell rate (%) |
|---|---|---|---|---|---|
| 81 | 300 | 0   | 0.42 | 0.16 | 72.4 |
| 82 | 300 | 100 | 1.65 | 0.39 | 80.9 |
| 83 | 300 | 200 | 3.02 | 0.59 | 83.7 |
| 84 | 300 | 400 | 2.17 | 0.32 | 87.1 |

As shown in Table 8, the trypan blue-negative viable cell count obtained with the use of collagenase alone (No. 81) was 0.42×10$^6$ cells. However, as a result of the addition of dispase, the viable cell count increased to 3.02×10$^6$ cells for 200 PU/ml dispase (No. 83), which was about 7 times that for collagenase alone. Meanwhile, there was no remarkable change in the trypan blue-positive dead cell count, and the obtained viable cell rate was 80% or more for each sample.

As shown in FIG. 11, the results of flow cytometry showed that the proportion of CD90-positive MSCs of interest was 90% or more either in the case of collagenase alone (No. 81) or in the case of the addition of dispase (Nos. 82-84), and the proportion of unnecessary CD324-positive epithelial cells was 10% or less in either case. The results in the case of collagenase alone (No. 81) differ from those in the case of collagenase alone (No. 1) in Example 1 (FIG. 3). This was probably because the manufacturer of collagenase used in Example 3 was different from that in Example 1.

TABLE 9

| No. | collagenase (CDU/ml) | dispase (PU/ml) | Viable cells (×10$^6$ cells/g) | CD90-positive MSC (%) | CD90-positive MSC (×10$^6$ cells/g) |
|---|---|---|---|---|---|
| 81 | 300 | 0   | 0.42 | 93.8 | 0.39 |
| 82 | 300 | 100 | 1.65 | 92.0 | 1.52 |
| 83 | 300 | 200 | 3.02 | 94.7 | 2.86 |
| 84 | 300 | 400 | 2.17 | 95.8 | 2.08 |

As shown in Table 9, the MSC count obtained for each sample was 0.39×10$^6$ cells in the case of collagenase alone (No. 81). However, as a result of the addition of dispase, the MSC count increased to 2.86×10$^6$ cells for 200 PU/ml dispase (No. 83), which was about 7 times that for No. 81.

As shown in FIG. 12, each enzyme-treated tissue remaining on the filter was subjected to HE staining for study. In the case of collagenase alone (No. 81), the extracellular matrix layer structure was maintained, indicating insufficient digestion. As a result of the addition of dispase, the extracellular matrix layer was digested. In the cases of 200 PU/ml dispase (No. 83) and 400 PU/ml dispase (No. 84), the extracellular matrix layer was completely digested.

These results of Example 6 revealed that the use of collagenase alone resulted in insufficient digestion of amnion; however, the addition of dispase to collagenase allowed the amnion to be digested in a concentration-dependent manner, and complete digestion of the extracellular matrix layer containing MSCs was observed with the use of dispase at a concentration of 2000 PU/ml or more.

Example 7

In view of Example 6, study was conducted in the above manner except that dispase was used without collagenase. Table 10 and FIGS. 13 and 14 show the results.

TABLE 10

| No. | dispase (PU/ml) | Viable cells (×10$^6$ cells/g) | Dead cells (×10$^6$ cells/g) | Viable cell rate (%) |
|---|---|---|---|---|
| 101 | 400  | 0.08 | 0.07 | 54.2 |
| 102 | 800  | 0.18 | 0.08 | 68.5 |
| 103 | 2000 | 0.95 | 0.38 | 71.1 |
| 104 | 4000 | 0.73 | 0.22 | 76.9 |

As shown Table 10, the cell count per 1 g of human amnion obtained after digestion with dispase alone increased in a thermolysin-concentration-dependent manner.

However, as shown in FIG. 13, the results of flow cytometry of cells contained in the enzyme treatment solution containing dispase alone indicated that the proportion of CD90-positive MSCs of interest was very small (a few %) at each concentration.

As shown in FIG. 14, as a result of study by HE staining of each enzyme-treated tissue remaining on the filter, it was found that the extracellular matrix layer containing MSCs was not digested at all, and destruction of the epithelial cell layer took place in a dispase-concentration-dependent manner.

These results of Example 7 revealed that no MSCs of interest are obtained with the use of dispase alone, and the epithelial cell layer is destroyed at a dispase concentration of 800 PU/ml or more.

Example 8

In view of Examples 6 and 7, the minimum necessary collagenase concentration for separation of amniotic mesenchymal stromal cells was studied at a fixed dispase concentration of 250 PU/ml. Table 11 and FIG. 15 show the results.

TABLE 11

| No. | collagenas (CDU/ml) | dispase (PU/ml) | Viable cells (×10⁶ cells/g) | Dead cells (×10⁶ cells/g) | Viable cell rate (%) | CD90-positive MSC (%) |
|---|---|---|---|---|---|---|
| 111 | 75 | 250 | 1.34 | 0.31 | 81.2 | 97.9 |
| 112 | 150 | 250 | 2.02 | 0.15 | 92.9 | 99.4 |
| 113 | 300 | 250 | 1.57 | 0.15 | 91.5 | 94.9 |

As shown in Table 11, the trypan blue-negative viable cell count obtained at a collagenase concentration of 300 CDU/ml (No. 113) was $1.57 \times 10^6$ cells. Meanwhile, when the collagenase concentration was a quarter (¼) of the above concentration (75 CDU/ml) (No. 113), the viable cell count decreased to $1.34 \times 10^6$ cells. There was no remarkable change in the trypan blue-positive dead cell count, and the obtained viable cell rate was 80% or more for each sample. In addition, the results of flow cytometry showed that the proportion of CD90-positive mesenchymal stromal cells was 90% or more for each sample.

As shown in FIG. 15, study was carried out by HE staining of each enzyme-treated tissue remaining on the filter. When the collagenase concentration was 300 CDU/ml (No. 113), only the epithelial cell layer was observed. Meanwhile, when the collagenase concentrations were 75 CDU/ml and 150 CDU/ml (Nos. 111 and 112, respectively), the extracellular matrix layer was observed, indicating insufficient digestion.

These results of Example 8 revealed that when the dispase concentration is fixed to 250 PU/ml, it is necessary to adjust the collagenase concentration to preferably at least 75 CDU/ml or more, more preferably 150 CDU/ml or more, and further preferably 300 CDU/ml or more for sufficient digestion of the extracellular matrix layer.

Example 9

Cells obtained in Example 1 were diluted with an αMEM culture solution supplemented with 10% FBS and seeded on a plastic dish, and adhesion culture of amnion-derived MSCs was carried out. The obtained cells were detached by trypsin treatment and subjected to trypsin neutralization with the use of an αMEM culture solution supplemented with 10% FBS, followed by centrifugation. Then, the supernatant was discarded and the obtained cell pellet was resuspended in RPMI1640 so as to prepare an amnion-derived MSC suspension. Cryopreservation solutions were prepared to have final compositions listed in Table 12 for the obtained suspension.

TABLE 12

|   |   | HES(%) | DMSO(%) | Human albumin (%) | Dextran 40 (%) |
|---|---|---|---|---|---|
| I | DMSO + HES + Alb | 6 | 5 | 4 | 0 |
| II | DMSO + HES | 6 | 5 | 0 | 0 |
| III | DMSO alone | 0 | 11 | 0 | 0 |
| IV | DMSO + Alb | 0 | 11 | 4 | 0 |
| V | ①:④ = 1:2 | 4 | 7 | 4 | 0 |
| VI | ①:④ = 2:1 | 2 | 9 | 4 | 0 |
| VII | DMSO + Dextran 40 | 0 | 11 | 0 | 2 |

DMSO: Simga-Aldrich Co. LLC.; Product No. D2650
HES: Nipro Corporation; Product No. HES40
Human albumin (Alb): Benesis Corporation, Albumin 25% Injection 12.5 g/50 ml
Dextran 40: Otsuka Pharmaceutical Factory, Inc., Low Molecular Dextran D Injection
Physiological saline: Otsuka Pharmaceutical Factory, Inc., used as a fluid for dilution.

Each cryopreservation solution was adjusted to contain amnion-derived MSCs at a concentration of $10^6$ cells/ml. Each solution (1 ml) was introduced into a cryotube and cooled in a program freezer to −40° C. at a freezing rate of −1 to −2° C./minute and further cooled to −90° C. at a freezing rate of −10° C./minute. Then, each cryotube was stored at −150° C. in an ultra-low temperature freezer. On the next day, each cryotube was immersed in a thermostatic bath at 37° C. for rapid thawing. Table 13 lists trypan blue-negative viable cell rates for rapidly thawed cells.

TABLE 13

|     |                  | Viable cell rate (%) |
| --- | ---------------- | -------------------- |
| I   | DMSO + HES + Alb | 93.2                 |
| II  | DMSO + HES       | 84.4                 |
| III | DMSO alone       | 55.1                 |
| IV  | DMSO + Alb       | 72.7                 |
| V   | 1:4 = 1:2        | 83.6                 |
| VI  | 1:4 = 2:1        | 94.5                 |
| VII | DMSO + Dextran 40| 82.6                 |

The above results revealed that the viable cell count was small in the case of DMSO alone (III), and the addition of HES, dextran, and/or albumin caused the viable cell rate to increase.

Further, each suspension of thawed cells (100 μL) was applied to 4 wells of a 24-well plate, 3 ml of an αMEM culture solution supplemented with 10% FBS was added, photos were taken 24 hours and 48 hours thereafter, and the average of cell count per visual field was determined. Table 14 and FIGS. 16 and 17 show the results.

TABLE 14

|     |                   | 24 hours later | | 48 hours later | |
| --- | ----------------- | -------------- | --- | -------------- | --- |
|     |                   | Cell count | Comparison with I (%) | Cell count | Comparison with I (%) |
| I   | DMSO + HES + Alb  | 208 ± 7   | 100  | 349 ± 40 | 100  |
| II  | DMSO + HES        | 180 ± 5   | 86.5 | 274 ± 21 | 78.5 |
| III | DMSO alone        | 103 ± 13  | 49.5 | 124 ± 24 | 35.5 |
| IV  | DMSO + Alb        | 88 ± 6    | 42.3 | 106 ± 17 | 30.4 |
| V   | ①:④ = 1:2         | 194 ± 14  | 93.2 | 297 ± 15 | 85.1 |
| VI  | ①:④ = 2:1         | 110 ± 8   | 52.9 | 187 ± 19 | 53.6 |
| VII | DMSO + Dextran 40 | 137 ± 46  | 65.9 | 156 ± 16 | 44.7 |

As shown in Table 13, cells proliferated slowly in the case of DMSO alone (III) or in the case of DMSO+Alb (IV). However, the addition of HES and/or dextran promoted cell proliferation. In particular, in the cases of I, II, and IV with decreased DMSO concentrations, remarkable cell proliferation was observed.

Example 10

Mice were subjected to allogeneic bone marrow transplantation and splenocyte transplantation to induce acute graft-versus-host disease (GVHD) for study of therapeutic effects of human amnion-derived MSC transplantation. 7- to 8-week-old female B6C3F1 mice were subjected to 15-Gy X-ray irradiation, followed by intravenous transplantation of allogeneic BDF1 mouse-derived bone marrow cells (1.0× $10^7$ cells) and splenocytes (3×$10^7$ cells). On days 14, 15, 17, and 21 after bone marrow cell transplantation, human amnion-derived MSCs (1×$10^5$ cells) obtained in the manner described in Example 1 (under conditions of 300 CDU/ml collagenase+250 PU/ml thermolysin) were intravenously transplanted. The body weight of each mouse was checked in a time-dependent manner. FIG. 18 shows the body weight change rate after bone marrow cell transplantation (based on the number of days elapsed).

The above results revealed that the delay of body weight increase due to acute graft-versus-host disease (GVHD) was improved as a result of human amnion-derived MSC transplantation.

Example 11

Rats were orally fed with dextran sodium sulfate (DSS) to induce inflammatory bowel disease for study of therapeutic effects of human amnion-derived MSC transplantation. Administration of 8% DSS with free oral liquid intake was started for 8-week-old male SD rats. On the next day of the start of DSS administration, human amnion-derived MSCs (1×$10^6$ cells) obtained in the manner described in Example 1 (under conditions of 300 CDU/ml collagenase+250 PU/ml thermolysin) were intravenously transplanted to each mouse, and DSS was administered for 5 days in total.

FIG. 19 shows disease activity (disease activity index (DAI): a score obtained based on body weight loss, stool texture, and rectal bleeding) and changes in the relative body weight. The results revealed that the pathological conditions of enteritis were improved as a result of human amnion-derived MSC transplantation.

Note that DAI scoring was conducted in accordance with the method described in Cooper, H. S.; Murthy, S. N.; Shah, R. S.; Sedergran, D. J. Clinicopathologic study of dextran sulfate sodium experimental murine colitis. Lab. Invest. 69:238-249; 1993.

Example 12

Pristane (2,6,10,14-tetramethyl-pentadecane) was administered to mice to induce systemic lupus erythematosus for study of therapeutic effects of human amnion-derived MSC transplantation. Pristane (500 μl) was intraperitoneally administered to 13-week-old male BALB/c mice. At the same time, human amnion-derived MSCs (1×$10^5$ cells/10 g) obtained in the manner described in Example 1 (under conditions of 300 CDU/ml collagenase+250 PU/ml thermolysin) were administered to each mouse via the tail vein. Thereafter, the same number of human amnion-derived MSCs were administered every two weeks. Twenty (20) weeks later, biochemical evaluation was conducted.

FIG. 20 shows time-dependent changes in urine protein. The results revealed that proteinuria associated with systemic lupus erythematosus was improved as a result of human amnion-derived MSC transplantation.

Example 13

Carbon tetrachloride ($CCl_4$) was repeatedly administered to rats to induce liver cirrhosis for study of therapeutic effects of human amnion-derived MSC transplantation. Intraperitoneal administration of $CCl_4$ (2 ml/kg) was carried out twice a week for 6-week-old male SD rats. In week 3 after the start of $CCl_4$ administration, human amnion-derived MSCs ($1 \times 10^6$ cells) obtained in the manner described in Example 1 (under conditions of 300 CDU/ml collagenase+250 PU/ml thermolysin) were intravenously transplanted to each rat. $CCl_4$ administration was administered for 7 weeks in total. Histological assessment of the liver was conducted.

FIG. 21 shows fibrosis area percentages (rates of collagen fiber-positive cells) obtained from the results of Masson trichrome staining of liver. The results revealed that hepatic fibrosis associated with liver cirrhosis was improved as a result of human amnion-derived MSC transplantation.

Example 14

Rats were subjected to radiation irradiation of the rectum to induce radiation enteritis for study of therapeutic effects of human amnion-derived MSCs. 8-week-old male SD rats received 5-Gy/day radiation irradiation on the lower abdomen for five consecutive days. On the last day of irradiation, human amnion-derived MSCs ($1 \times 10^6$ cells) obtained in the manner described in Example 1 (under conditions of 300 CDU/ml collagenase+250 PU/ml thermolysin) were intravenously transplanted to each rat. Three (3) days later, histological evaluation of the rectum was conducted.

FIG. 22 shows PAS-positive goblet cell counts (/HPF: count per high power field) obtained via rectal PAS staining. The results revealed that reduction of goblet cells due to radiation enteritis was improved as a result of human amnion-derived MSC transplantation.

REFERENCE SIGNS LIST

1 Mesenchymal stem cells
2 Epithelial cell layer
3 Extracellular matrix layer

The invention claimed is:

1. A method for producing a cultured mesenchymal cell composition, the method comprising:
  treating an amnion with collagenase and at least one of thermolysin and dispase, thereby obtaining mesenchymal cells;
  cryopreserving a mixture obtained by mixing a solution comprising dimethylsulfoxide and hydroxyethyl starch or dextran with a mesenchymal cell composition comprising obtained mesenchymal cells, thereby obtaining a cryopreserved mixture;
  thawing the cryopreserved mixture, thereby obtaining a thawed mixture; and subsequently
  culturing the thawed mixture, thereby obtaining the cultured mesenchymal cell composition.

2. The method according to claim 1, wherein in the treating, a concentration of the collagenase is from 50 CDU/ml to 1000 CDU/ml, and a concentration of the at least one of thermolysin and dispase is from 100 PU/ml to 800 PU/ml.

3. The method according to claim 1, wherein the treating is performed at from 30° C. to 40° C. for at least 30 minutes.

4. The method according to claim 1, wherein the treating is performed while stirring the amnion, the collagenase, and the at least one of thermolysin and dispase with a stirrer or shaker at from 10 rpm/minute to 100 rpm/minute for at least 30 minutes.

5. The method according to claim 1, wherein the treating is performed such that an epithelial cell layer comprising a basal membrane is not digested and an extracellular matrix layer comprising the mesenchymal cells is digested.

6. The method according to claim 1, wherein the mesenchymal cell composition comprises 20% or less of CD324-positive epithelial cells and at least 75% of CD90-positive cells.

7. The method according to claim 1, further comprising:
  filtering the amnion treated with the collagenase and the at least one of thermolysin and dispase through a mesh.

8. The method according to claim 7, wherein the filtering is performed such that an epithelial cell layer containing a basal membrane remains on the mesh and the mesenchymal cells pass through the mesh.

9. The method according to claim 7, wherein a pore size of the mesh is from 40 to 200 μm.

10. The method according to claim 7, wherein the filtering is performed such that the mesenchymal cells pass through the mesh in a free fall motion.

11. The method according to claim 7, further comprising:
  recovering mesenchymal cells that have passed through the mesh; and
  culturing recovered mesenchymal cells.

12. The method according to claim 11, wherein the recovering comprises diluting a filtrate comprising the mesenchymal cells that have passed through the mesh with a medium or balanced salt solution, and centrifuging a diluted filtrate.

13. The method according to claim 11, wherein in the culturing of the recovered mesenchymal cells, the recovered mesenchymal cells are cultured in a medium comprising from more than 0.05% by mass to 5% by mass of albumin.

14. The method according to claim 1, wherein the solution comprising dimethylsulfoxide and hydroxyethyl starch or dextran further comprises albumin.

15. A therapeutic method, comprising:
  administering a cultured mesenchymal cell composition obtained by the method according to claim 1 to a patient in need thereof.

16. The therapeutic method according to claim 15, wherein the cultured mesenchymal cell composition is injected to the patient.

17. The therapeutic method according to claim 15, wherein the therapeutic method is a method for treating at least one disease selected from the group consisting of a graft-versus-host disease, an inflammatory bowel disease, systemic lupus erythematosus, liver cirrhosis, and radiation enteritis.

* * * * *